(12) United States Patent
Nishikiori et al.

(10) Patent No.: US 7,951,330 B2
(45) Date of Patent: May 31, 2011

(54) CLINICAL SPECIMEN PROCESSING APPARATUS

(75) Inventors: Mizuho Nishikiori, Kobe (JP);
Masayasu Sento, Kobe (JP); Mitsuo Yamasaki, Itami (JP); Hideyuki Higuchi, Kobe (JP)

(73) Assignee: Sysmex Corporation, Hyogo (JP)

( * ) Notice: Subject to any disclaimer, the term of this patent is extended or adjusted under 35 U.S.C. 154(b) by 172 days.

(21) Appl. No.: 11/168,595

(22) Filed: Jun. 28, 2005

(65) Prior Publication Data
US 2006/0024200 A1 Feb. 2, 2006

(30) Foreign Application Priority Data

Jun. 29, 2004 (JP) .................. 2004-191094
Jun. 29, 2004 (JP) .................. 2004-191107

(51) Int. Cl.
*G01N 21/00* (2006.01)
*G01N 35/02* (2006.01)
*G01N 31/00* (2006.01)
*G05B 21/00* (2006.01)

(52) U.S. Cl. ............... 422/67; 422/63; 422/64; 422/65; 422/66; 436/43; 436/46; 436/50; 700/19; 700/266

(58) Field of Classification Search .............. 422/63, 422/65, 67; 436/43, 46, 50; 700/266, 19; 3/63, 65, 67
See application file for complete search history.

(56) References Cited

U.S. PATENT DOCUMENTS

| | | | |
|---|---|---|---|
| 5,209,903 A * | 5/1993 | Kanamori et al. .............. 422/65 |
| 5,629,207 A * | 5/1997 | Seto et al. ...................... 436/50 |
| 5,779,982 A | 7/1998 | Aota et al. |
| 5,854,075 A | 12/1998 | Levine et al. |
| 6,456,944 B1 | 9/2002 | Burkhardt et al. |
| 6,629,060 B2 | 9/2003 | Okuno et al. |
| 7,487,061 B2 | 2/2009 | Biwa |
| 2002/0020233 A1 * | 2/2002 | Baba et al. ................. 73/864.16 |
| 2002/0128801 A1 | 9/2002 | Okuno et al. |
| 2003/0220761 A1 | 11/2003 | Biwa |
| 2005/0281707 A1 * | 12/2005 | Nakaya et al. .................. 422/63 |

FOREIGN PATENT DOCUMENTS

| | | |
|---|---|---|
| EP | 0417006 A2 | 3/1991 |
| EP | 0990908 A1 | 4/2000 |
| EP | 1391734 A2 | 2/2004 |
| JP | 08-304414 A | 11/1996 |
| JP | 09-274044 A | 10/1997 |
| JP | 10-10136 * | 1/1998 |

(Continued)

OTHER PUBLICATIONS

European Search Report for Application No. 05013720.7 dated Jan. 15, 2007.

*Primary Examiner* — Jill Warden
*Assistant Examiner* — Neil Turk
(74) *Attorney, Agent, or Firm* — Brinks Hofer Gilson & Lione

(57) ABSTRACT

The clinical specimen processing apparatus is provided with a discharge pipette and supply pipette for staining in conjunction a blood smear sample preparation operation, a top sensor for detecting whether or not the operations of raising the discharge pipette and supply pipette are performed normally, and a controller for re-executing the operations of raising the discharge pipette and supply pipette based on the top sensor detecting that the operations of raising the discharge pipette and supply pipette are not performed normally.

13 Claims, 21 Drawing Sheets

FOREIGN PATENT DOCUMENTS

| | | | |
|---|---|---|---|
| JP | 10-010136 A | 1/1998 |
| JP | 10-308737 | 11/1998 |
| JP | 10-308737 A | 11/1998 |
| JP | 2001-38657 | * 2/2001 |
| JP | 2003-080487 A | 3/2003 |
| JP | 2003-114233 A | 4/2003 |
| JP | 2004-004105 A | 1/2004 |
| JP | 2004-045396 A | 2/2004 |
| WO | WO 01/68259 A1 | 9/2001 |

* cited by examiner

Automatic retry of the raising operation of the discharge pipette and supply pipette

FIG.21

| | 501 | 502 | 503 | 504 | 505 |
|---|---|---|---|---|---|
| | No. | ID | Date | Time | ErrorCode |
| | 153 | SP-1000I^13713^11001 | 2004/2/21 | 16:15:39 | 113005 |
| | 154 | SP-1000I^13713^11002 | 2004/2/21 | 16:20:12 | 161100 |
| | 155 | SP-1000I^13713^11001 | 2004/2/21 | 16:35:22 | 113005 |

FIG.22

| 511 | 512 | 513 | 514 |
|---|---|---|---|
| Date | Time | Segment | Count |
| 2004/2/21 | 16:15:39 | 1 | 12345 |
| 2004/2/21 | 16:20:12 | 2 | 12346 |
| 2004/2/21 | 16:35:22 | 3 | 12347 |

FIG.23

| Date | Time | Information |
|---|---|---|
| 2004/2/21 | 16:15:39 | 13 |
| 2004/2/21 | 16:20:12 | 16 |
| 2004/2/21 | 16:35:22 | 12 |

521 — Date
522 — Time
523 — Information

CLINICAL SPECIMEN PROCESSING APPARATUS

This application claims priority under 35 U.S.C. §119 to Japanese Patent Application Nos. 2004-191094 and 2004-191107 both filed Jun. 29, 2004, the entire contents of which are hereby incorporated herein by reference.

FIELD OF THE INVENTION

The present invention relates to a clinical specimen processing apparatus, and specifically relates to a clinical specimen processing apparatus provided with an operating member for performing operations in conjunction with a test sample treating operation.

BACKGROUND

Conventional smear sample preparation devices for preparing smear samples of blood specimens are known among clinical specimen processing apparatuses (for example, refer to Japanese Laid-Open Patent Publication No. 8-271390). An automatic sample preparing device for automatically preparing slide glasses from blood smear to staining process using a plurality of operating members is disclosed in Japanese Laid-Open Patent Publication No. 8-271390. In the automatic sample preparing device disclosed in Japanese Laid-Open Patent Publication No. 8-271390, for example, a motor is used to move pipettes (operating member) in vertical directions to suction and discharge staining solution and cleaning solution in the staining process performed in the staining unit. In the conventional automatic sample preparing device disclosed in Japanese Laid-Open Patent Publication No. 8-271390, when, for example, the operation of raising the pipette in the staining unit using a motor is performed abnormally for any reason, the device generally shuts down immediately. In this way a conventional clinical specimen processing apparatus indiscriminately halts the operation of the entire apparatus when an operation is not performed normally, regardless of the type of operation.

Therefore, a conventional clinical specimen processing apparatus is not convenient and cannot perform processing suitable for the type of operation since the entire apparatus is indiscriminately shut down when an operation is not performed normally.

SUMMARY

The scope of the present invention is defined solely by the appended claims, and is not to any degree affected by the statements within this summary.

In order to solve the previously described problem, an object of the present invention is to provide a clinical specimen processing apparatus capable of performing processing suitable for the operation when an operation is not performed normally.

The first aspect of the present invention relates to a clinical specimen processing apparatus comprising a mechanism for performing an operation to process a clinical specimen, a detection means for detecting whether or not the operation is performed normally by the mechanism, and a controller for executing processing corresponding to the operation when the detection means detects that the operation of the mechanism has not been performed normally, and wherein the controller re-executes the abnormally performed operation when the operation belongs to a previously set first group.

The second aspect of the present invention relates to a clinical specimen processing apparatus provided with a mechanism for performing operations to process a clinical specimen; a detection means for detecting whether or not an operation is performed normally by the mechanism; and a controller for controlling the operation of the mechanism; and wherein the operation of the mechanism is classified beforehand as errors which stop the operation when an operation has not been performed normally, and retries which execute the same operation again when an operation has not been performed normally; and the controller stops the operation of the mechanism when the detection means detects that an operation belonging to the errors has not been performed normally, and re-executes the operation when the detection means detects that an operation belonging to the retries has not been performed normally.

BRIEF DESCRIPTION OF THE DRAWINGS

FIG. 21 is a table showing the error log content in attached file of FIG. 20;

FIG. 22 is a table showing the operation count content in the attached file of FIG. 20; and FIG. 23 is a table showing the maintenance parts and replaced parts log in the attached file of FIG. 20.

DETAILED DESCRIPTION OF THE EMBODIMENTS

The embodiments of the present invention are described hereinafter with reference to the drawings.

First Embodiment

Figure 1:
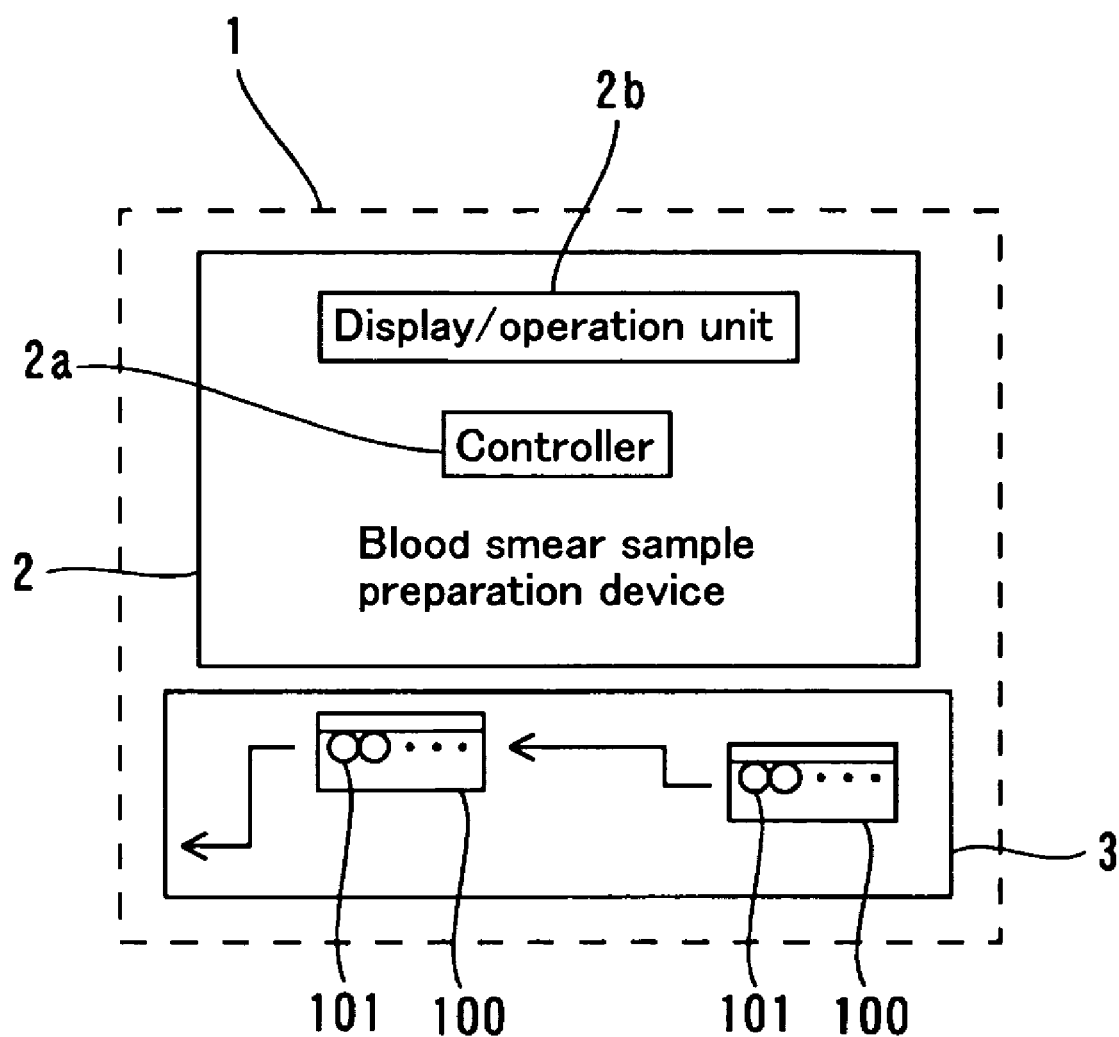
FIG. 1 is a block diagram showing the clinical specimen processing apparatus of a first embodiment of the present invention.
Figure 2:
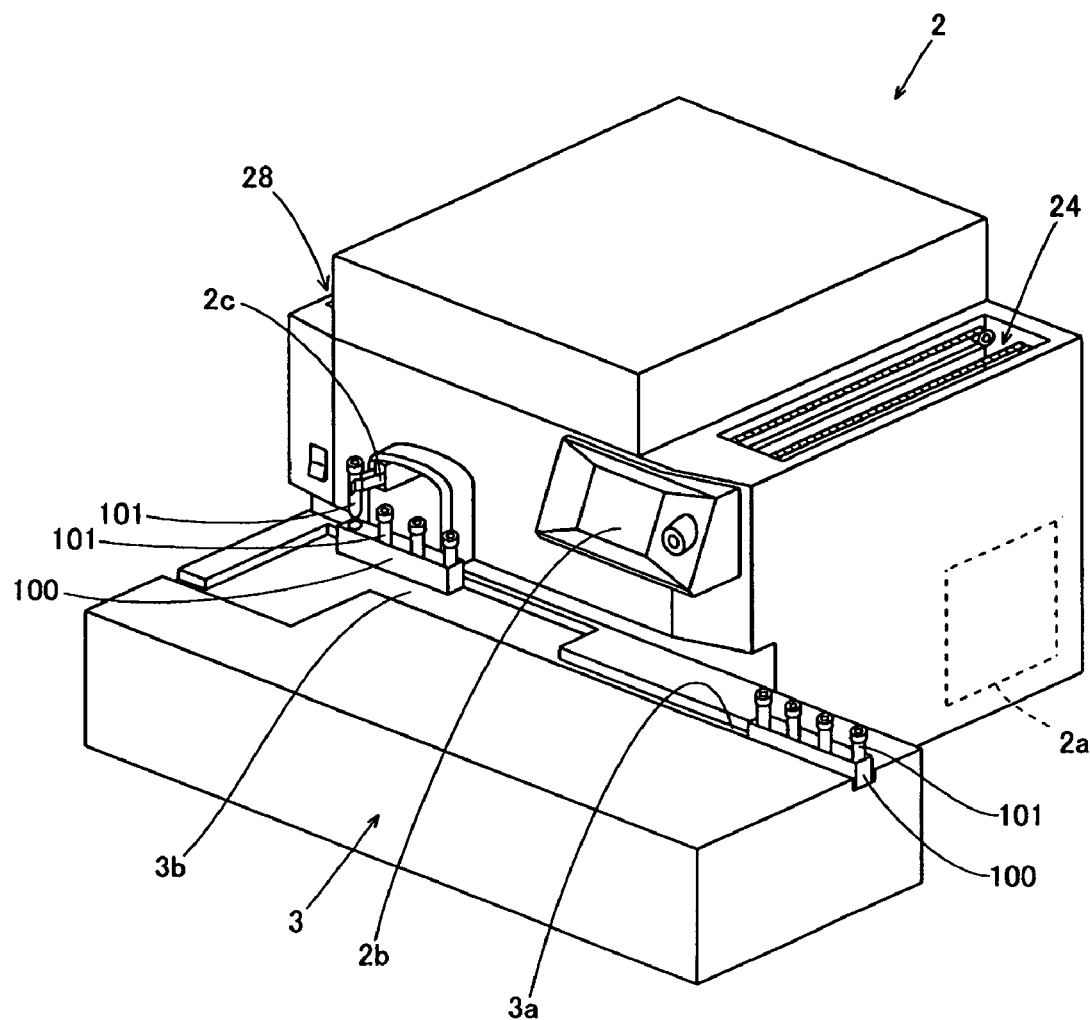
FIG. 2 is a perspective view showing the blood smear preparation device and conveyance device of the clinical specimen processing apparatus of the first embodiment shown in FIG. 1.
Figure 3:
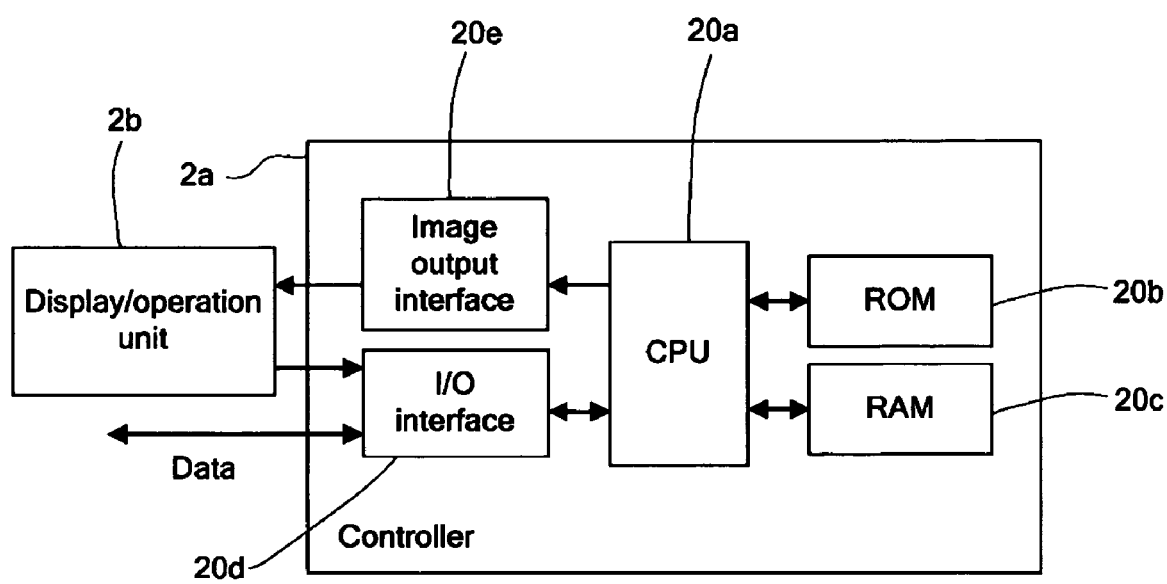
FIG. 3 is a block diagram showing the structure of the blood smear preparation device shown in FIG. 1.
Figure 4:
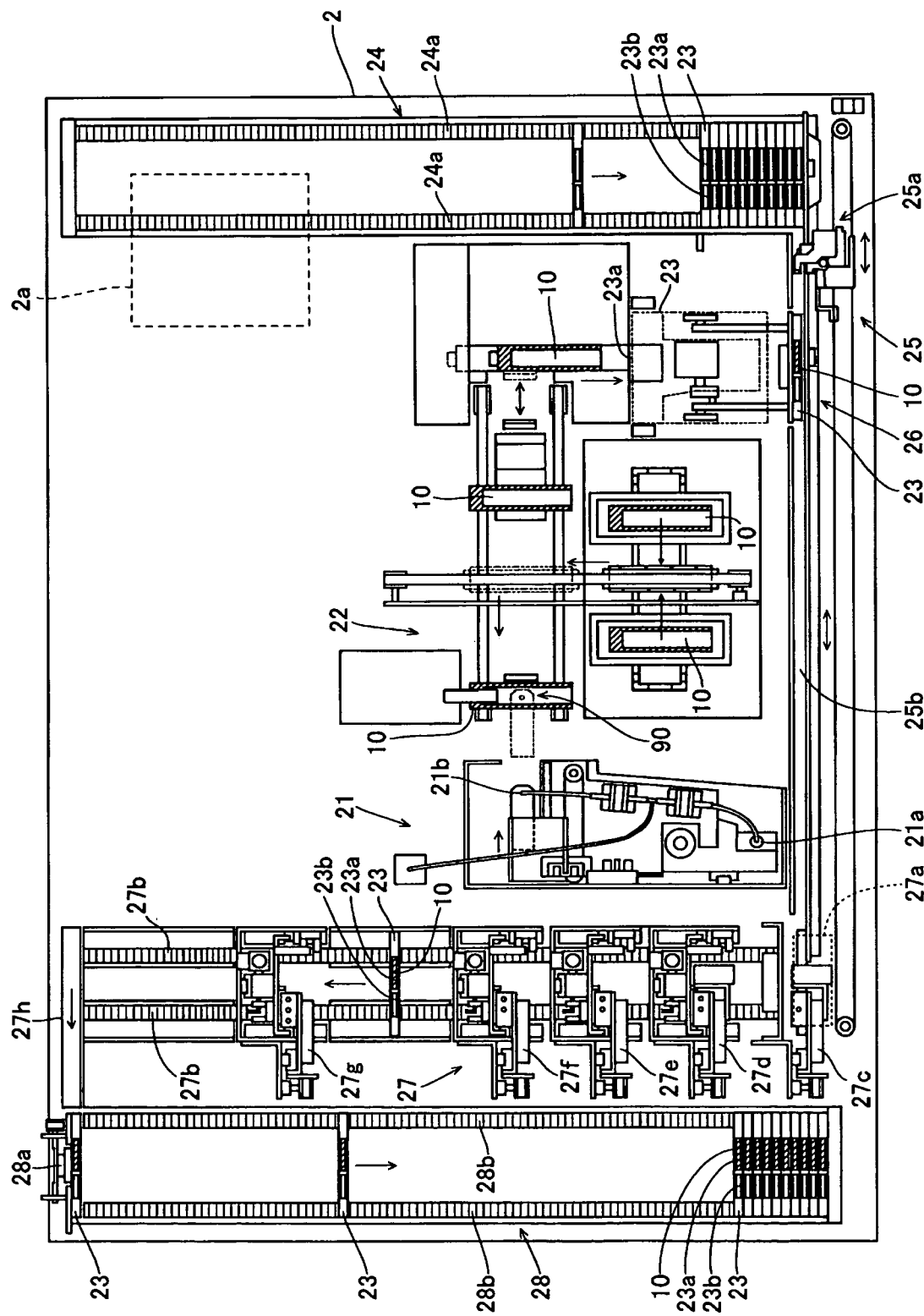
FIG. 4 is a top view showing the internal structure of the blood smear preparation device of FIG. 2.

FIG. 1 is a block diagram of the clinical specimen processing apparatus of a first embodiment of the present invention. FIG. 2 is a perspective view of the blood smear sample preparation device and conveyance device in the clinical specimen processing apparatus of FIG. 1, FIG. 3 is a block diagram showing the structure of the blood smear sample preparation device of FIG. 1, and FIG. 4 is a top view showing the internal structure of the blood smear sample preparation device of FIG. 2. FIGS. 5 through 8 illustrate the structure and operation of the third suction/discharge mechanism of the staining unit of the blood smear sample preparation device, and FIGS. 9 through 12 illustrate the structure and operation of the storage feed mechanism of the blood smear sample preparation device.

The general structure of the clinical specimen processing apparatus 1 of a first embodiment is described below with reference to FIGS. 1 and 2. The clinical specimen processing apparatus 1 of the first embodiment is provided with a blood smear sample preparation device 2 and a conveyance device 3, as shown in FIG. 1.

The blood smear sample preparation device 2 is provided to prepare smear samples from blood specimens. The blood smear sample preparation device 2 includes a controller 2a, and touch panel-type display/operation unit 2b. As shown in FIG. 3, the controller 2a of the blood smear sample preparation device 2 is provided with a CPU 20a, ROM 20b, RAM 20c, I/O interface 20d, and image output interface 20e. The ROM 20b stores an operating system, control program for controlling the operation of the device, and data necessary for the execution of the control program. The CPU 20a is capable of loading the control program in the RAM 20c, or executing the control program directly from the ROM 20b. Thus, the data processed by the CPU 20a are transmitted through the I/O interface 20d to each part of the device or to an external device, and data required for the processing by the CPU 20a are received through the I/O interface 20d from each part of the device or from external devices. The CPU 20a displays an error message on the display/operation unit 2b when an error is generated as described later. The CPU 20a executes the control program to perform normal control of the smear sample preparation operation of the blood smear sample preparation device 2, control the retry operation and return-to-origin operation in conjunction with the normal smear sample preparation operation of the blood smear sample preparation device 2, and determine an abnormal (error) state in the blood smear sample preparation device 2.

Furthermore, the conveyance device 3 is provided on the front of the blood smear sample preparation device 2, and has an input unit 3a and pick-up unit 3b, as shown in FIG. 3. The conveyance device 2 is provided to automatically transport a sample rack 100, which accommodates test tubes 101 containing blood, to the blood smear sample preparation device 2.

The general structure of the blood smear sample preparation device and the conveyance device are described below with reference to FIGS. 2 through 12. As shown in FIG. 2, the blood smear sample preparation device 2, in addition to the controller 2a and display/operation unit 2b, is provided with a hand member 2c for transporting the test tubes 101 containing blood from the conveyance device 3 side to the blood smear sample preparation device 2 side. The blood smear sample preparation device 2 is further provided with a suction dispensing mechanism 21, smear unit 22, resin cassette 23, cassette holder 24, cassette conveyor 25, slide glass insert unit 26, staining unit 27, and storage unit 28, as shown in FIG. 4.

The suction/dispensing mechanism 21 has the functions of suctioning blood from a test tube 101 which has been transported to the blood smear sample preparation device 2 side by the hand member 2c (refer to FIG. 2), and titrating the suctioned blood onto a slide glass 10. The suction-dispensing mechanism 21 includes a piercer (aspiration needle) 21a for suctioning blood from a test tube 101, and a dispensing pipette 21b for dispensing the suctioned blood on the slide glass 10, as shown in FIG. 4.

Figure 5:
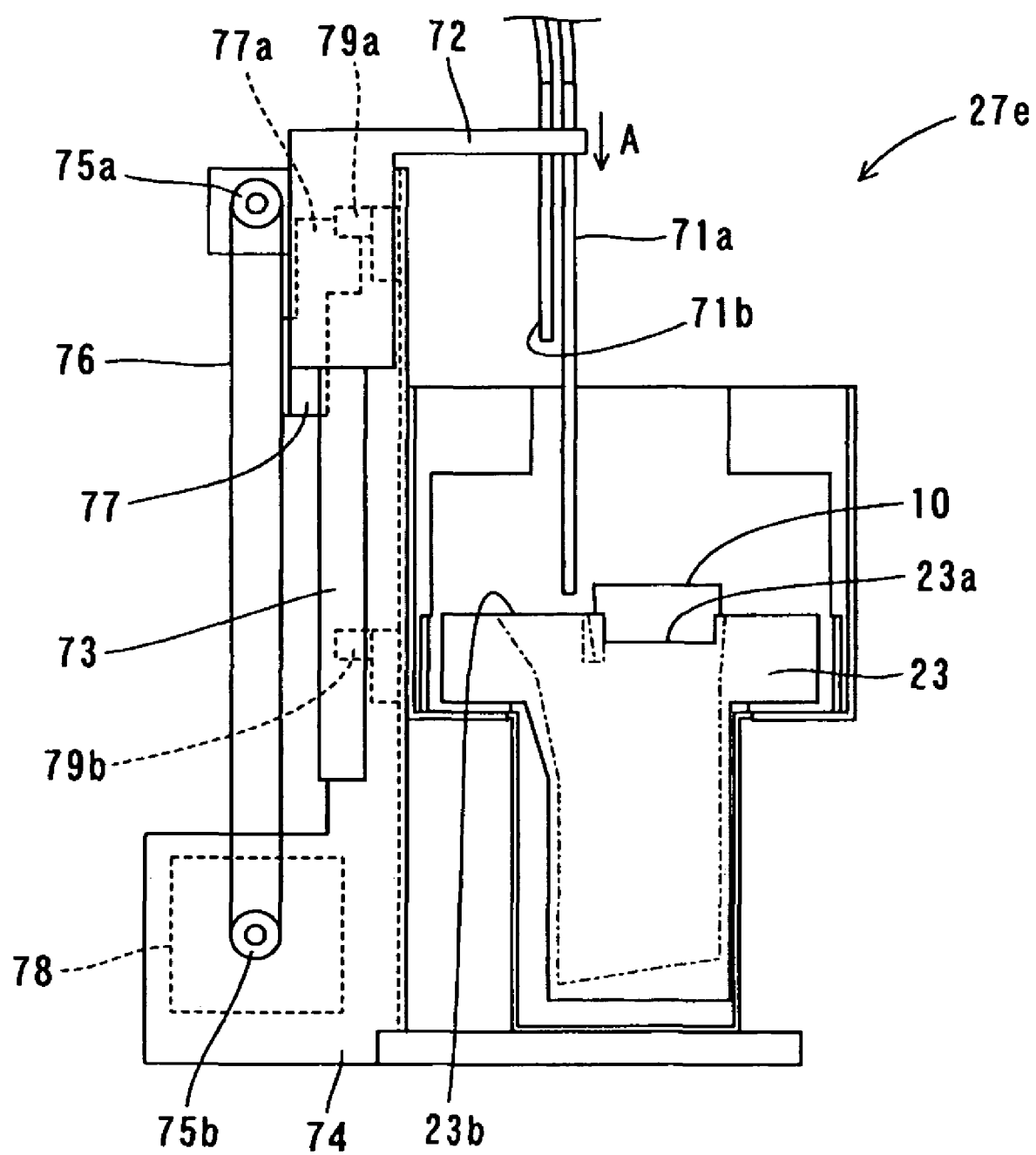
FIG. 5 is a top view showing the third suction/discharge part of the staining unit of the blood smear preparation device of FIG. 4.

The smear unit 22 is provided to supply a slide glass 10 to the dispensing/smear position 90, dry the blood smear of the blood titrated on the slide glass 10, and print on the slide glass 10, as shown in FIG. 4. The resin cassette 23 is structured so as to be capable of accommodating slide glass 10 with smear and the fluid (staining solution) used in the staining process. As shown in FIG. 4, the cassette 23 includes a slide glass hole 23a, and stain suction/dispensing hole 23b. The slide glass hole 23a and the stain suction/dispensing hole 23b have internally plentiful as shown in FIG. 5.

The cassette holder 24 is provided to input the cassette 23 to the cassette conveyor 25, and includes a conveyor belt 24a, as shown in FIG. 4. The cassette conveyor 25 is provided to transport a cassette 23 inserted from the cassette holder 24 to the slide glass input unit 26 and staining unit 27. The cassette conveyor 25 includes a cassette conveyor member 25a which is movable in horizontal directions, and a transport path 25b for transporting a cassette 23 supplied from the cassette holder 24, as shown in FIG. 4. The slide glass input unit 26 is provided accommodating a slide glass 10, which has been stained and printed, in the slide glass hole 23a of the cassette 23, as shown in FIG. 4.

The staining unit 27 is provided to perform a staining process on the smeared slide glass 10 by supplying and discharging staining solution to the stain suction/dispensing hole 23b of a cassette 23 delivered by the cassette conveyance member 25a. As shown in FIG. 4, the staining unit 27 includes a take-up mechanism 27a for taking the cassette 23 delivered by the cassette conveyance member 25a to the staining unit 27, conveyor belt 27b for transporting the cassette 23 delivered from the take-up mechanism 27a, first through fifth suction/discharge units 27c~27g for supplying and discharging staining solution to the cassette 23, and a delivery mechanism 27h for delivering the cassette 23 from the conveyor belt 27b to the conveyor belt 28b side of the storage unit 28. The take-up mechanism 27a of the staining unit 27 has a structure identical to that of the input mechanism 28a of the storage unit 28 described later.

The structure of the first suction/discharge unit 27c through fifth suction/discharge unit 27g of the staining unit 27 is described below using the example of the third suction/discharge unit 27e while referring to FIGS. 5.about.8. As shown in FIGS. 5.about.8, the third suction-discharge unit 27e includes a first object, such as discharge pipette 71a, for suctioning and discharging staining solution within the cassette 23, a second object, such as supply pipette 71b, for supplying staining solution within the cassette 23, pipette support member 72 for supporting the discharge pipette 71a and discharge pipette 71b, frame 74 for mounting the pipette support member 72 through the direct-action guide 73, set of pulleys 75a and 75b mounted on the frame 74 at predetermined spacing in a vertical direction, drive belt 76 on which are installed the set of pulleys 75a and 75b, linkage member 77 which links the drive belt 76 and pipette support member 72, and pulse motor 78 (refer to FIGS. 6 and 8) for driving the rotation of the pulley 75b.

Figure 6:
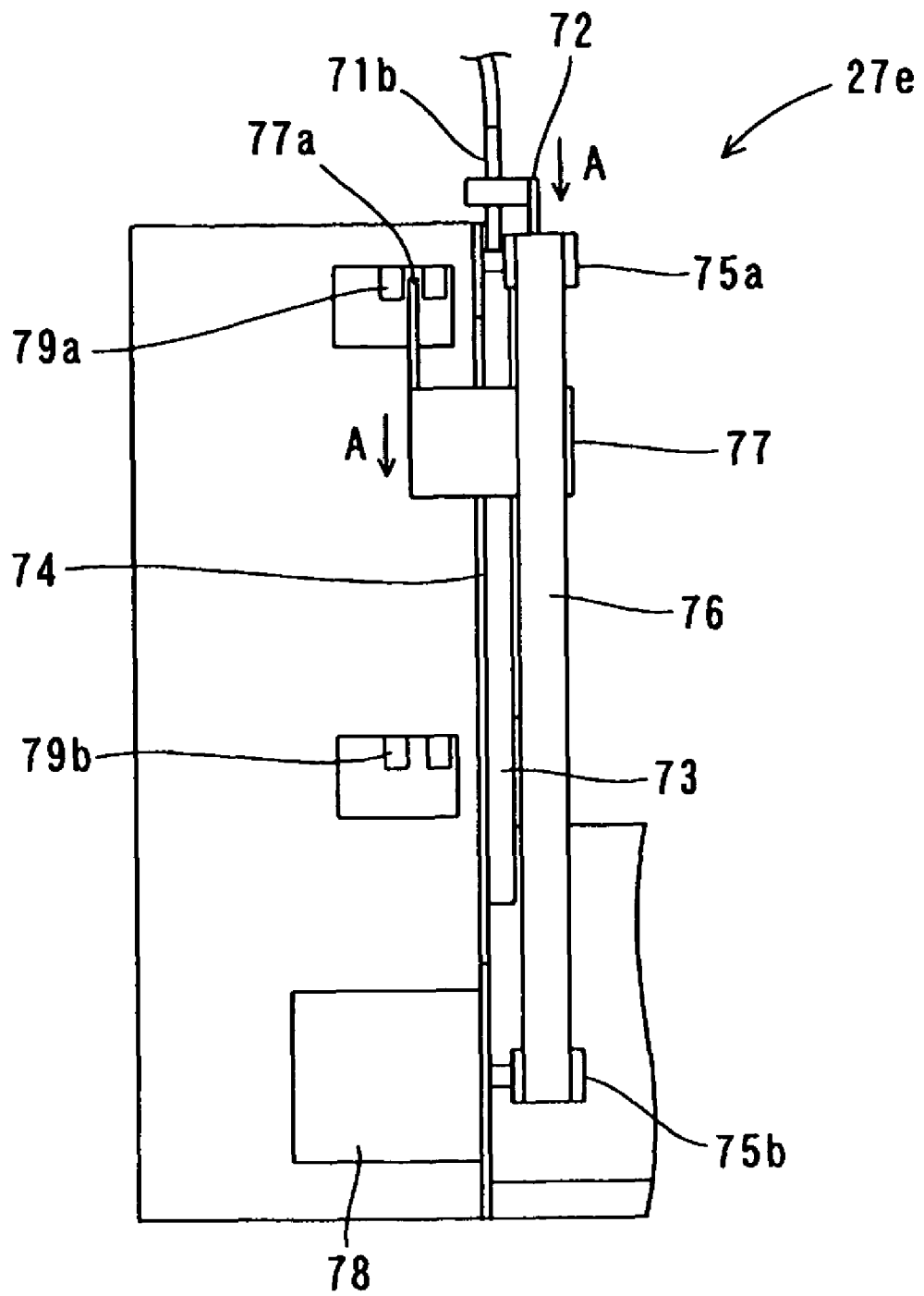
FIG. 6 is a left side view of the third suction/discharge part of the staining unit of FIG. 5.
Figure 7:
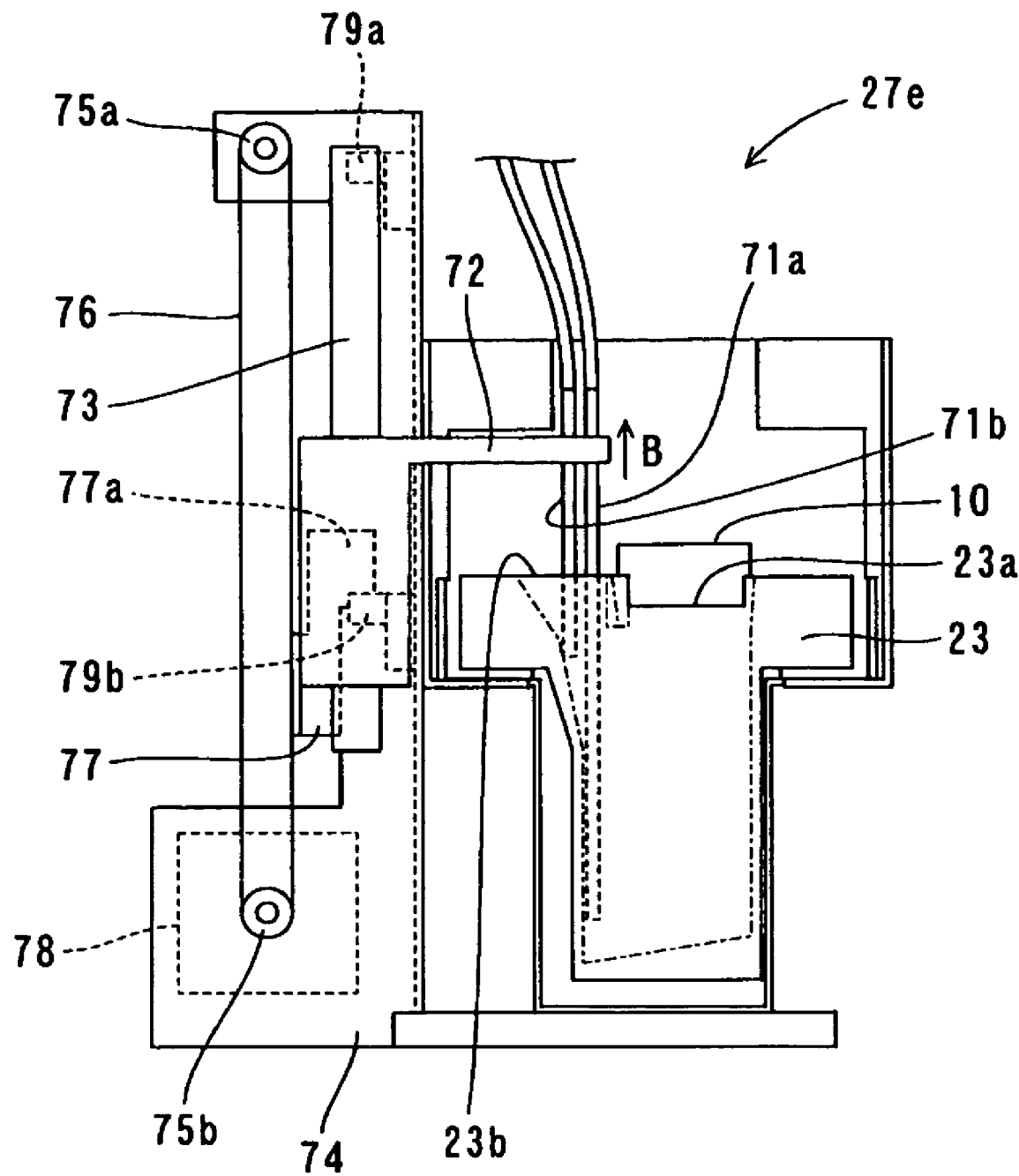
FIG. 7 is a top view showing the lowering of the pipette support member in the third suction/discharge part of the staining unit of FIG. 5.
Figure 8:
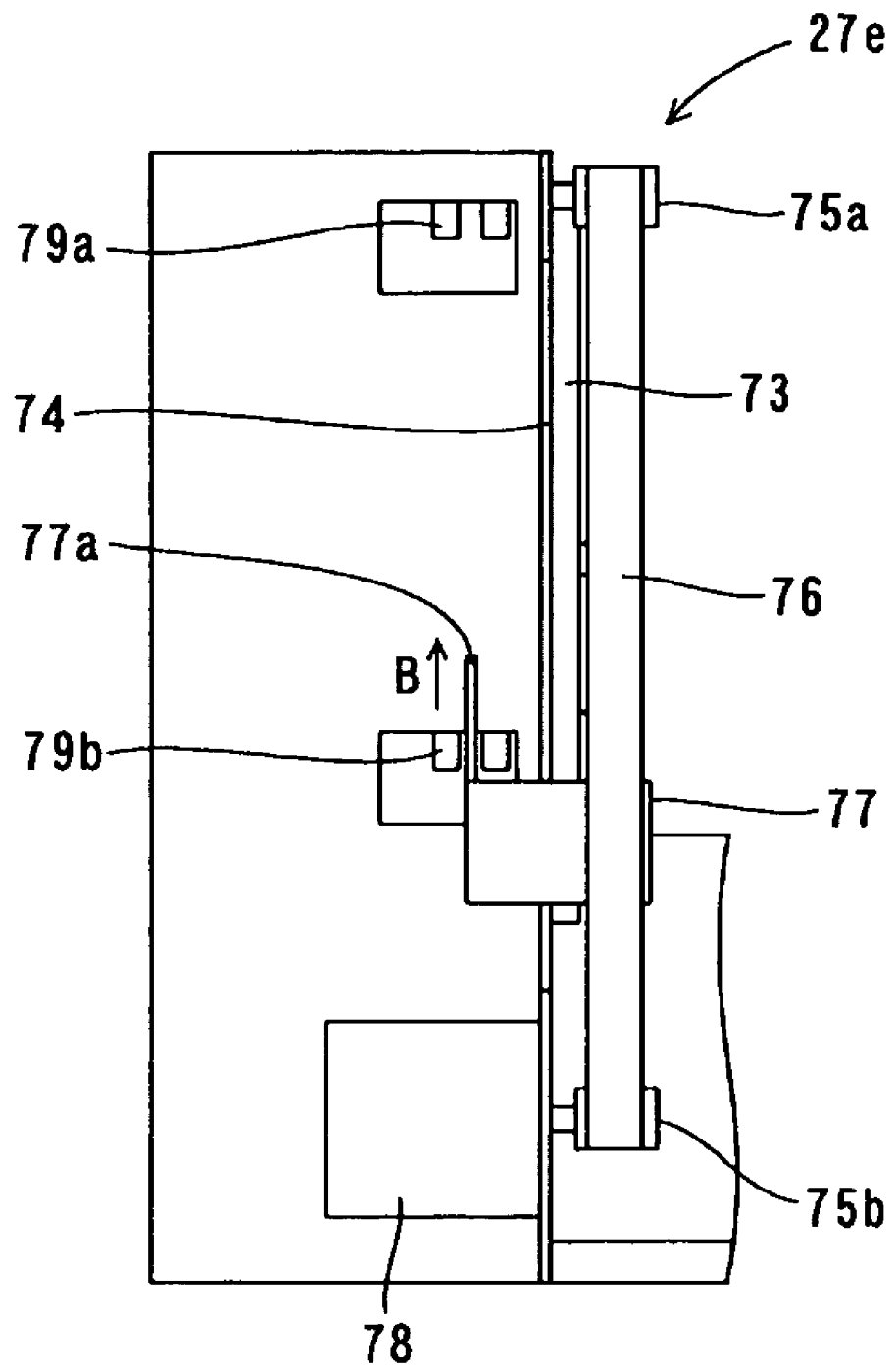
FIG. 8 is a left side view of the third suction/discharge part of the staining unit of FIG. 7.

As shown in FIGS. 6 and 8, a detection piece 77a is integratedly provided on the linkage member 77, which links the drive belt 76 and pipette support member 72, so as to extend from the back side of the frame 74 to detect the top end position and bottom end position of the pipette support member 72. Mounted on the back side of the frame 74 are a top sensor 79a of the light-transmitting type for detecting the arrival of the detection piece 77a at the top end position, and a bottom sensor 79b of the light-transmitting type for detecting the arrival of the detection piece 77a at the bottom end position. The third suction-discharge unit 27e moves the discharge pipette 71a and the supply pipette 71b downward, and thereafter provide suction/discharge and supply of staining solution to the cassette 23.

The storage unit 28 is provided for the storage of the cassettes 23 which accommodate slide glasses 10 stained by the staining unit 27. As shown in FIG. 4, the storage unit 28 is provided with an input mechanism 28a for feeding a cassette 23 delivered from the conveyor belt 27b by the delivery mechanism 27h of the staining unit 27 to the conveyor belt 28b of the storage unit 28, and a conveyor belt 28b for transporting a cassette 23 delivered from the input mechanism 28a.

Figure 9:
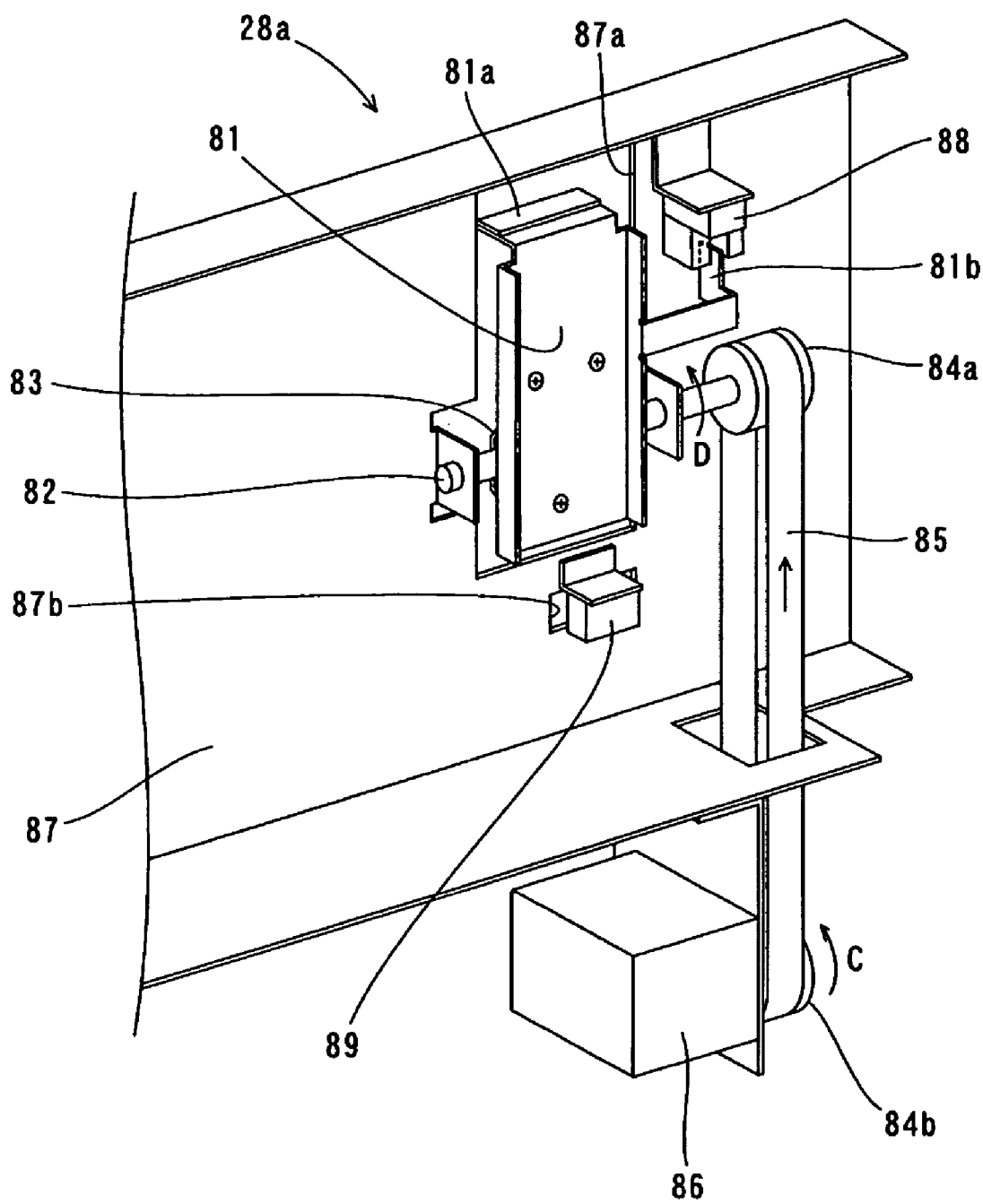
FIG. 9 is a perspective view showing the feed mechanism of the storage unit of the blood smear sample preparation device of FIG. 4.

The structure of the input mechanism 28a of the storage unit 28 is described below with reference to FIGS. 9~12. As shown in FIG. 9, the input mechanism 28a includes a third object, such as an oscillating member 81, support shaft 82 which supports the oscillating member 81, mounting member 83 for mounting the oscillating member 81 on the support shaft 82, pulley 84a mounted on one end of the support shaft 82, pulley 84b provided at a predetermined spacing relative to the pulley 84a, drive belt 85 which is installed on the set of pulleys 84a and 84b, pulse motor 86 for driving the rotation of the pulley 84b, and frame 87 for mounting the support shaft 82 and pulse motor 86.

Figure 10:
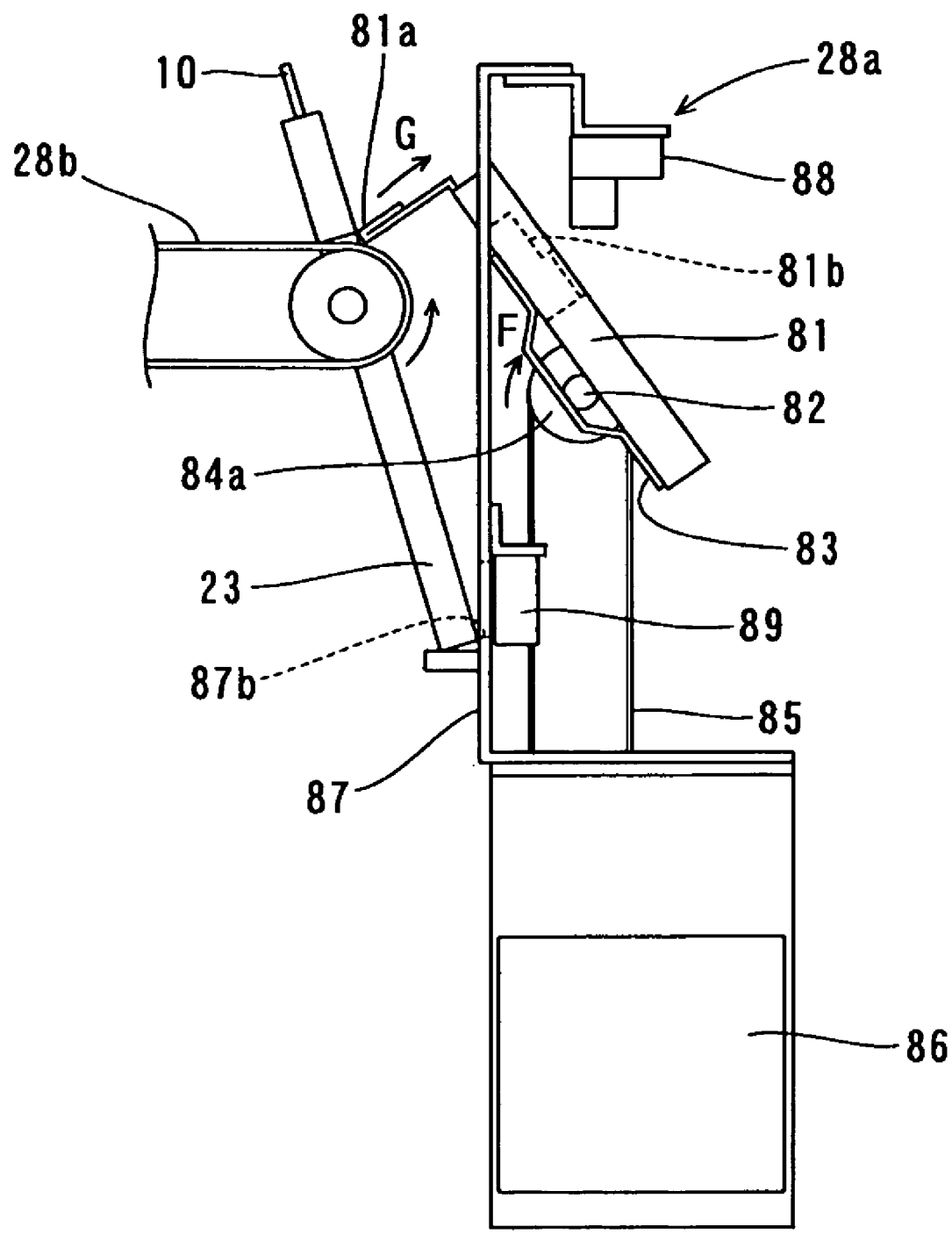
FIG. 10 illustrates the operation of the storage feed mechanism of FIG. 9.
Figure 11:
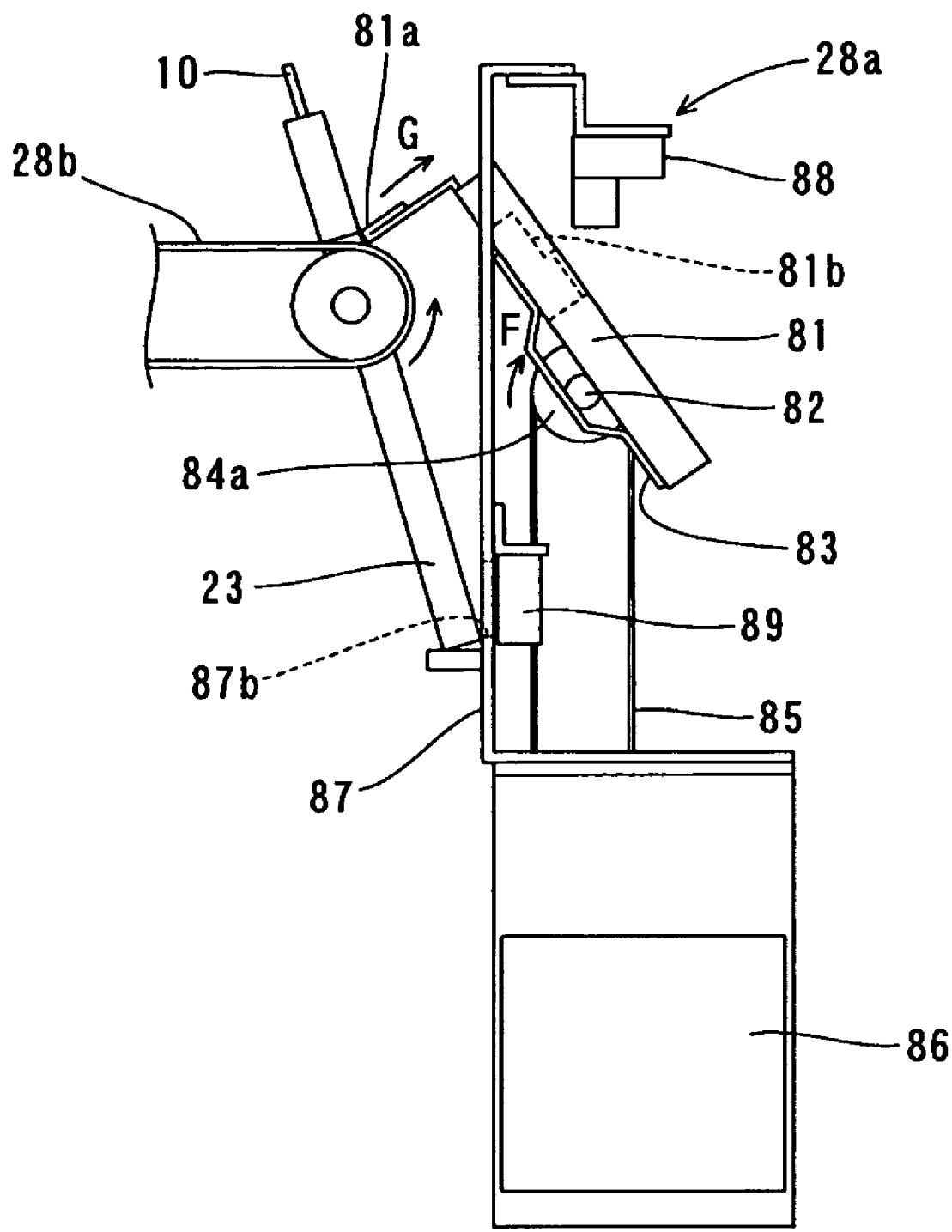
FIG. 11 illustrates the operation of the storage feed mechanism of FIG. 9.
Figure 12:
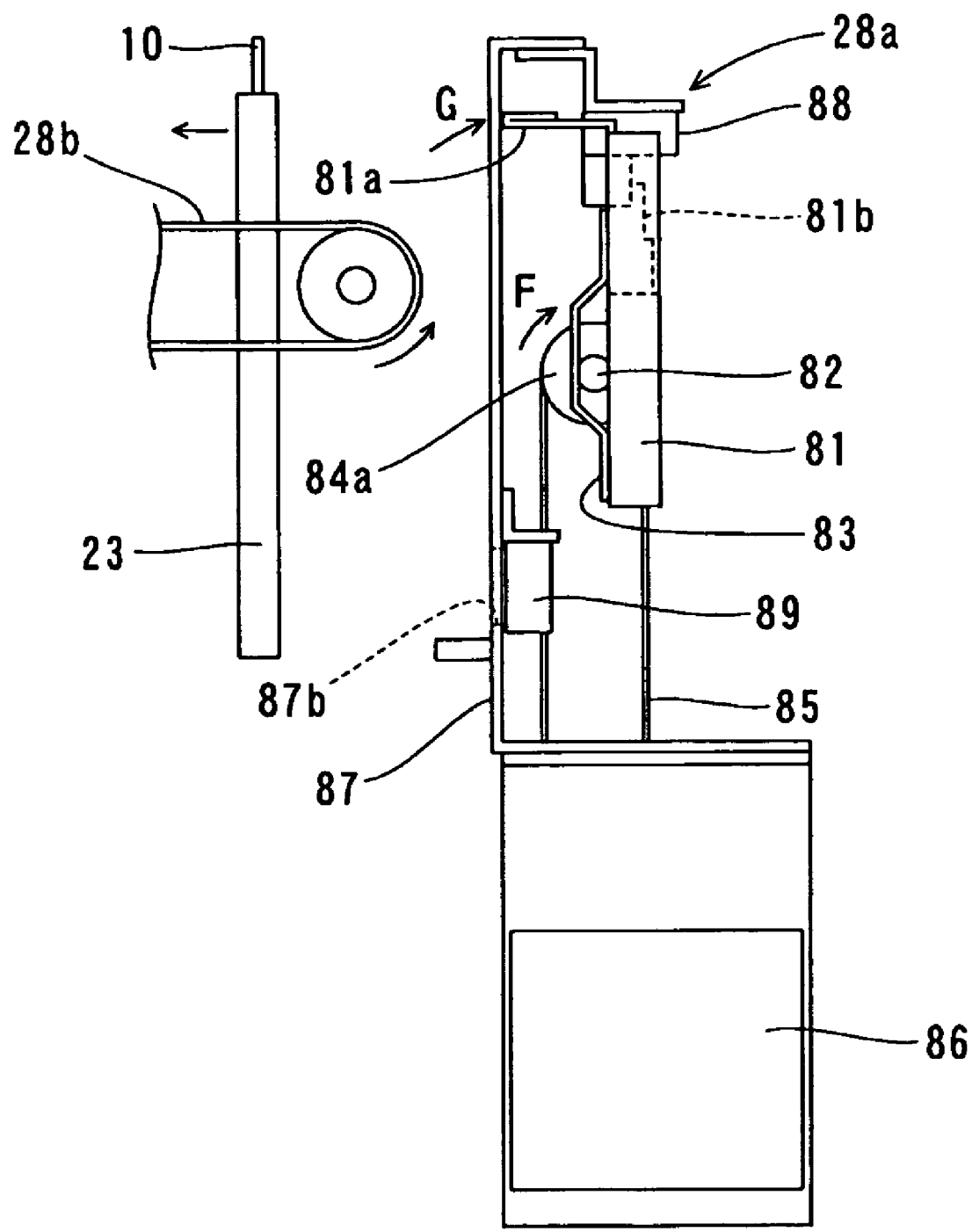
FIG. 12 illustrates the operation of the storage feed mechanism of FIG. 9.

As shown in FIGS. 10~12, the oscillating member 81 is provided to apply pressure on the top back surface of the cassette 23 as it oscillates. As shown in FIG. 9, a pressing part 81a which presses against the top back surface of the cassette 23, and a detection piece 81b for detecting the oscillating member 81 at the origin position (non-oscillated position) are integratedly provided on the oscillating member 81. As shown in FIG. 9, mounted on the frame 87 are a sensor 88 of the light-transmitting type for detecting the detection piece 81b of the oscillating member 81, and a sensor 89 of the light-reflecting type for detecting whether or not the cassette 23 (refer to FIG. 10) has been delivered normally onto the conveyor belt 28b by the input mechanism 28a. As shown in FIG. 9, provided on the frame 87 are an opening 87a through which the oscillating member 81 extends to the conveyor belt 28b side when oscillated, and an opening 87b through which the light passes from the sensor 89 of the light-reflecting type.

The operation of the clinical specimen processing apparatus 1 of the first embodiment is described below with reference to FIGS. 1~14. First, clinical chart information of the provider of the specimen (patient) is input to a host computer not shown in the drawings. Then, the information is transmitted from the host computer to the blood smear sample preparation device 2, and the blood smear sample preparation device 2 shown in FIGS. 1 and 2 collects the blood specimen from a test tube 101 held in the specimen rack 100 transported by the conveyance device 3, and prepares a blood smear sample.

When the blood smear sample is prepared by the blood smear sample preparation device 2, first, as a suction-dispensing operation shown in FIG. 2, the hand member 2c of the blood smear sample preparation device 2 raises and mixes the test tube 101 of the specimen rack 100 which has been transported from the input unit 3a of the conveyance device 3 to the pick-up unit 3b, and thereafter the test tube 101 is deposited in the suction-dispensing mechanism 21 shown in FIG. 4. Next, the blood is suctioned from inside the test tube 101 by the piercer 21a. After the blood suctioning operation ends, the dispensing pipette 21b is moved to the dispensing/smear position 90 shown in FIG. 4, and blood is titrated (dispensed) from the dispensing pipette 21b to the slide glass 10.

A smear operation is performed by the smear unit 22 in parallel with the suctioning/dispensing operation or after the suction/dispensing operation performed by the suction/dispensing mechanism 21. In the smear unit 22, a slide glass 10 is supplied to the dispensing/smear position 90 (refer to FIG. 4), and the dispensed blood on the slide glass 10 is dried. After the printing the specimen information on the slide glass 10, the printed slide glass 10 is moved to the slide glass insertion unit 26.

Next, the cassette 23, which sits in the cassette holder 24 shown in FIG. 4, is delivered to the transport path 25b of the cassette conveyor 25 by the conveyor belt 24a. Then, the cassette 23 is transported to the slide glass insertion unit 26 by the cassette conveyance member 25a. After the operation of inserting the slide glass 10 in the cassette 23 by the slide glass insertion unit 26, the cassette 23, which contains the smeared slide glass 10, is transported to the staining unit 27 by the cassette conveyance member 25a.

In the staining unit 27 of the first embodiment, the cassette 23 transported by the cassette conveyance member 25a is delivered on to the conveyor belt 27b by the take-up unit 27a, and transported to the conveyor belt 27b. In the first suction/discharge units 27c through fifth suction/discharge unit 27g, staining solution and aqueous cleaning solution are sequentially dispensed, suctioned and discharged through the stain suction/dispensing hole 23b of the cassette 23, so as to perform a staining process on the smeared slide glass 10 of the cassette 23. Details of the delivery operation of the cassette 23 by the take-up mechanism 27a are identical to the cassette 23 delivery operation by the input mechanism 28a of the storage unit 28 described later.

The operation of the third suction/discharge unit 27e, among operations of the first suction/discharge units 27c through fifth suction/discharge unit 27g, is described in terms of the lowering operation and raising operation of the discharge pipette 71a and supply pipette 71b mounted on the pipette support member 72 with reference to FIGS. 5~8. First, the pulse motor 78 is driven in rotation in a predetermined direction when the pulse motor 78 receives a pulse signal from the controller 2a from the state shown in FIGS. 5 and 6. In this way the drive force of the pulse motor 78 is transmitted through the pulley 75b and drive belt 76 to the linkage member 77, and the linkage member 77 and pipette support member 72 are moved downward (arrow A direction in FIGS. 5 and 6). At this time, as the discharge pipette 71a and the supply pipette 71b move downward together with the pipette support member 72, the pipettes 71a and 71b are inserted into the cassette 23 through the stain suction/dispensing hole 23b of the cassette 23. Then, the pulse motor 78 stops when the number of pulse signals received by the pulse motor 78 from the controller 2a attains a standard number of pulses, and the lower position of the discharge pipette 71a and supply pipette 71b are confirmed when the bottom sensor 79b detects the detection piece 77a of the linkage member 77. Thus ends the operation of lowering the discharge pipette 71a and supply pipette 71b mounted on the pipette support member 72.

Subsequently, after staining solution has been suctioned and discharged into the cassette 23 by the discharge pipette 71a, another staining solution is supplied into the cassette 23 by the supply pipette 71b. Next, the pipette support member 72 is raised (direction B in FIGS. 7 and 8) from the state shown in FIGS. 7 and 8 by driving the rotation of the pulse motor 78 in the reverse direction of the previously mentioned predetermined direction by means of pulse signals sent from the controller 2a to the pulse motor 78. In this way the discharge pipette 71a and supply pipette 71b are removed from inside the cassette 23. As shown in FIGS. 5 and 6, the drive of the pulse motor 78 is stopped when the top sensor 79a detects the detection piece 77a of the linkage member 77. Thus ends the operation of raising the discharge pipette 71a and supply pipette 71b mounted on the pipette support member 72. The lowering operation and raising operation of the discharge pipette 71a and supply pipette 71b are controlled by the controller 2a of the blood smear sample preparation device 2.

In the first embodiment, the raising operation is repeated once again in a retry operation when the operation of raising the discharge pipette 71a and supply pipette 71b is not accomplished normally. In the operation of the clinical specimen processing apparatus, there are, for example, instances in which continued operation of the apparatus after an abnormal operation may result in a breakdown; however, there are also instances (error criteria) in which there is a very low possibility of performing an operation normally even after repeated operations (retries) once an operational error occurs, but there are also instances (retry criteria) in which there is a high possibility of successful operation after an operation has failed once. For example, the raising operation of the discharge pipette 71a and supply pipette 71b may not be performed normally when slippage is generated between the pulley 75b and drive belt 76 or the pipettes 71a or 71b become caught on the cassette 23. However, normal operation often results when a retry operation eliminates the slippage between the pulley 75b and drive belt 76 or releases the pipettes 71a and 71b from the cassette 23. For example, the operation of lowering the discharge pipette 71a and supply pipette 71b may not be performed normally if the progress of the operation is impaired by the pipettes 71a or 71b touching other components of the cassette 23. When the retry operation is executed in this instance the pipette 71a or 71b may be damaged through contact with the cassette 23. The blood smear sample preparation device 2 of the present embodiment classifies operations as error criteria and retry criteria beforehand, and detects whether or not each operation is performed normally by sensors such as the top sensor 79a and the like, so as to stop the operation (smear sample preparation operation) of the entire device when an error criteria operation is not performed normally, and execute a retry operation when a retry criteria operation is not performed normally.

Figure 13:
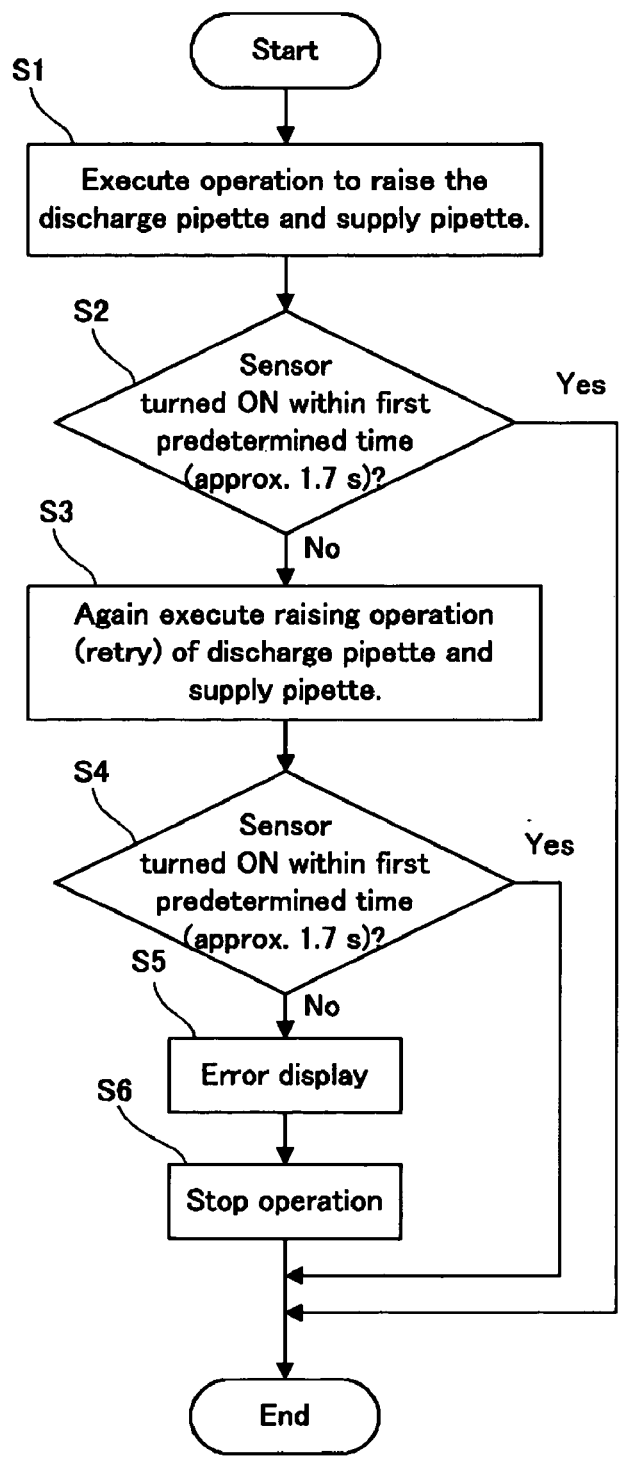
FIG. 13 is a flow chart illustrating automatic retries in the operation of raising the discharge pipette and supply pipette mounted on the pipette support member of the staining unit in FIG. 5.
Figure 14:
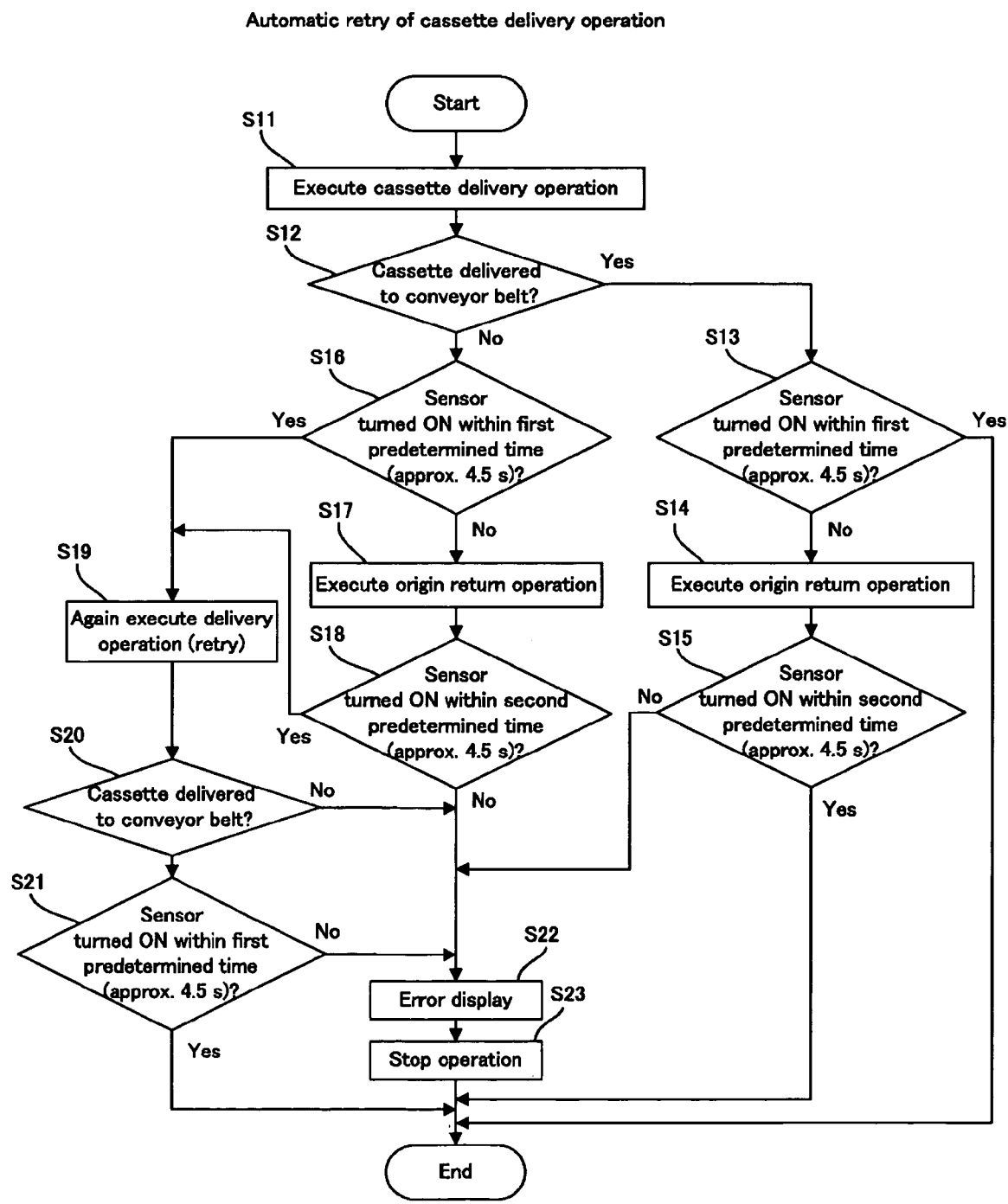
FIG. 14 is a flow chart illustrating the automatic retries of the cassette feed operation by the oscillating member of the storage feed mechanism of FIG. 9.

The retry operation of the operation for raising the discharge pipette 71a and the supply pipette 71b is described in detail below with reference to the flow chart of FIG. 13. The retry operation below is controlled by the controller 2a of the blood smear sample preparation device 2. First, the CPU 20a provides pulse signals to the pulse motor 78 to perform the operation of raising the discharge pipette 71a and supply pipette 71b (step S1). Thereafter, the CPU 20a determines whether or not the top sensor 79a is turned ON after a predetermined time (approximately 1.7 seconds) from the start of the raising operation of the discharge pipette 71a and supply pipette 71b (step S2). When the top sensor 79a is turned ON after a predetermined time has elapsed (approximately 1.7 seconds) after the start of the raising operation (step S2: YES), the CPU 20a directly continues the smear sample preparation operation.

When the top sensor 79a is not turned ON after a predetermined time has elapsed (approximately 1.7 seconds) after the start of the raising operation (step S2: NO), the CPU 20a again performed the raising operation (retry operation) of the pipettes 71a and 71b (step S3). Specifically, the operation of re-raising the discharge pipette 71a and supply pipette 71b is accomplished by sending pulse signals from the controller 2a to the pulse motor 78. Subsequently, the CPU 20a determines whether or not the top sensor 79a is turned ON after a predetermined time (approximately 1.7 seconds) has elapsed after the start of the re-raising operation (retry operation) (step S4). When the top sensor 79a is turned ON after a first predetermined time has elapsed (approximately 1.7 seconds) after the start of the re-raising operation (retry operation) (step S4: YES), the CPU 20a directly continues the smear sample preparation operation. When, however, the top sensor 79a is not turned ON after a first predetermined time has elapsed (approximately 1.7 seconds) after the start of the re-raising operation (retry operation) (step S4: NO), the CPU 20a determines that the raising operation of the discharge pipette 71a and supply pipette 71b is abnormal (error), and an error display is executed for the raising operation of the discharge pipette 71a and supply pipette 71b on the display/operation unit 26 of the blood smear sample preparation device 2 (step S5), and the blood smear sample preparation operation is stopped (step S6), and the process ends.

The lowering operation of the discharge pipette 71a and supply pipette 71b is classified as error criteria. Whether or not this operation is performed normally can be detected by detecting whether or not the top sensor 79a is turned OFF after a predetermined time has elapsed after the start of the operation. When an abnormal operation is detected, the controller 2a executes an error display for the lowering operation of the discharge pipette 71a and supply pipette 71b, and the smear sample preparation operation is stopped.

When the smear sample preparation operation continues, after the raising operation of the discharge pipette 71a and supply pipette 71b, the cassette 23 which contains the smeared slide glass 10 is sequentially transported from the conveyor belt 27b to the conveyor belt 28b side of the storage unit 28 by the delivery mechanism 27h shown in FIG. 4. Then, the cassette 23 is forwarded to the conveyor belt 28b of the storage unit 28 by the input mechanism 28a of the storage unit 28.

The operation of delivering the cassette 23 to the conveyor belt 28b by the oscillating member 81 of the input mechanism 28a is described below with reference to FIGS. 9~12. First, from the state shown in FIGS. 9 and 10, the pulse motor 86 is rotated in the arrow C direction of FIG. 9 when the pulse motor 86 received pulse signals from the controller 2a. In this way the drive force of the pulse motor 86 is transmitted to the support shaft 82 through the pulley 84b, drive belt 85, and pulley 84a. Therefore, since the support shaft 82 is rotated in the arrow D direction in FIGS. 9 and 10, the oscillating member 81 mounted on the support shaft 82 is rotated in the arrow E direction in FIG. 10. In this way the oscillating piece 81a at the top of the oscillating member 81 is pressed against the top back surface of the cassette 23, as shown in FIG. 11. The cassette 23 is then moved to the conveyor belt 28b side and deposited on the conveyor belt 28b, as shown in FIG. 12, by the pressing of the oscillating piece 81a of the oscillating member 81. At this time, whether or not the cassette 23 has been moved normally onto the conveyor belt 28b is detected by the sensor 89 of the light-reflecting type mounted on the frame 87. Thereafter, the support shaft 82 is rotated in the arrow F direction in FIGS. 11 and 12 by means of the rotation of the pulse motor in the reverse direction to the arrow C direction of FIG. 9. In this way the oscillating member 81 mounted on the support shaft 82 is rotated in the arrow G direction in FIGS. 11 and 12. As shown in FIGS. 9 and 10, the rotation of the pulse motor 86 is stopped when the detection piece 81b of the oscillating member 81 is detected by the sensor 88. Therefore, the oscillating member 81 is returned to the origin position, and the operation of delivering the cassette 23 by the oscillating member 81 of the input mechanism 28a ends. The operation of delivering the cassette 23 onto the conveyor belt 28b by the oscillating member 81 of the input mechanism 28a is controlled by the controller 2a of the blood smear sample preparation device 2.

In the first embodiment, when the operation of delivering the cassette 23 to the conveyor belt 28b by the oscillating member 81 of the input mechanism 28a is not performed normally, the same delivery operation is performed once again. The retry operation by the input mechanism 28a is described in detail below with reference to the flow chart of FIG. 14. The retry operation below is accomplished by the controller 2a of the blood smear sample preparation device 2. First, the CPU 20a performs an operation to deliver the cassette 23 to the conveyor belt 28b via the oscillating member 81 by sending pulse signals to the pulse motor 86 (step S11). Then, the CPU 20a determines whether or not the cassette 23 has been delivered to the conveyor belt 28b (step S12). When the cassette 23 has been delivered to the conveyor belt 28b in step S12 (step S12: YES), the CPU 20a discriminates whether or not the sensor 88 is turned ON by detecting the detection piece 81b of the oscillating member 81 after a first predetermined time (approximately 4.5 seconds) has elapsed after the start of the cassette 23 delivery operation (step S13). When the sensor 88 is turned ON after a first predetermined time (approximately 4.5 seconds) has elapsed after the start of the cassette 23 delivery operation in step S13 (step S13: YES), the smear sample preparation operation continues directly. When, however, the sensor 88 is not turned ON after a first predetermined time (approximately 4.5 seconds) has elapsed after the start of the cassette 23 delivery operation (step S13: NO), the CPU 20a performs an operation to return the oscillating member 81 to the origin position by sending pulse signals to the pulse motor 86 (step S14). The CPU 20a determines whether or not the sensor 88 is turned ON by detecting the detection piece 81b of the oscillating member 81 after a second predetermined time (approximately 4.5 seconds) has elapsed after the start of the operation to return the oscillating member 81 to the origin position (step S15). When the sensor 88 is turned ON after a second predetermined time (approximately 4.5 seconds) has elapsed after the start of the operation to return the oscillating member 81 to the origin position in step S15 (step S15: YES), the smear sample preparation operation continues directly. When, however, the sensor 88 is not turned ON after a second predetermined time (approximately 4.5 seconds) has elapsed after the start of the operation to return the oscillating member 81 to the origin position in step S15 (step S15: NO), the CPU 20a does not perform a retry operation, and determines that the cassette 23 delivery operation by the oscillating member 81 is abnormal (error), and executes an error display for the cassette 23 delivery operation by the oscillating member 81 on the display/operation unit 2b of the blood smear sample preparation device 2 (step S22), then stops the smear sample preparation operation (step S23), and the process ends.

When the cassette 23 is not delivered to the conveyor belt 28b in step S12 (step S12: NO), the CPU 20a determines whether or not the sensor 88 is turned ON after a first predetermined time (approximately 4.5 second) has elapsed from the start of the cassette 23 delivery operation (step S16). When the sensor 88 is turned ON after a first predetermined time (approximately 4.5 seconds) has elapsed after the start of the cassette 23 delivery operation in step S16 (step S16: YES), the CPU 20a advances the process to step S19, and again performs the cassette 23 delivery operation (retry operation) to the conveyor belt 28b by the oscillating member 81. Specifically, the retry operation is performed by the oscillating member 81 when the controller 2a again sends pulse signals to the pulse motor 86. When, however, the sensor 88 is not turned ON after a first predetermined time has elapsed (approximately 4.5 seconds) from the start of the cassette 23 delivery operation in step S16 (step S16: NO), the CPU 20a returns the oscillating member 81 to the origin position by sending pulse signals to the pulse motor 86 (step S17). Then, the CPU 20a determines whether or not the sensor ** has been turned ON after a second predetermined time (approximately 4.5 seconds) has elapsed from the start of the operation to return the oscillating member 81 to the origin position (step S18). When the sensor 88 has not been turned ON after a second predetermined time (approximately 4.5 seconds) has elapsed from the start of the operation to return the oscillating member 81 to the origin position (step S18: NO), the CPU 20a advances to step S22, displays an error message, and stops the smear sample preparation operation. When the sensor 88 is turned ON after a second predetermined time (approximately 4.5 seconds) has elapsed from the start of the operation to return the oscillating member 81 to the origin position in step S18 (step S18: YES), the CPU 20a advances to step S19, and performs the retry operation.

Thereafter, the CPU 20a determines whether or not the cassette 23 has been delivered to the conveyor belt 28b (step S20). When the cassette 23 has not been delivered onto the conveyor belt 28b in step S20 (step S20: NO), the CPU 20a advances to step S22, displays an error message, and stops the smear sample preparation operation. When the cassette 23 has been delivered onto the conveyor belt 28b in step S20 (step S20: YES), the CPU 20a determines whether or not the sensor 88 is turned ON after a first predetermined time (approximately 4.5 seconds) has elapsed from the start of the cassette 23 redelivery operation (retry operation) (step S21). When the sensor 88 has been turned ON after a first predetermined time (approximately 4.5 seconds) has elapsed from the start of the cassette redelivery operation (retry operation) in step S21 (step S21: YES), the CPU 20a directly continues the smear sample preparation operation. When, however, the sensor 88 has not been turned ON after the first predetermined time (approximately 4.5 seconds) has elapsed since the start of the cassette 23 redelivery operation (retry operation) in step S21 (step S21: NO), the CPU 20a advances to step S22, an error message is displayed, and the smear sample preparation operation is halted.

When the smear sample preparation operation continues, thereafter the cassette 23, which has been delivered from the input mechanism 28a, is transported to the storage unit 28 by the conveyor belt 28b, and stored therein.

In the first embodiment, the retry operation can be executed normally since the retry operation eliminates the cause for the abnormal execution of the first operation by performing the retry operation by re-executing the same operation in the case of abnormal execution of the operation to raise the discharge pipette 71a and supply pipette 71b and the operation to deliver the cassette 23 onto the conveyor belt 28b. In this way the device is stopped a fewer number of times compared to when the device is stopped immediately the first time an operation is performed abnormally, since the smear sample preparation operation of the blood smear sample preparation device 2 of the clinical specimen processing apparatus 1 is performed continuously without stopping. As a result, sample processing time is faster, and the workload on the user performing the recovery process is lessened. Furthermore, when the retry operation cannot be executed normally, the user can quickly confirm the retry operation has been not been performed normally by providing the display/operation unit 2b for displaying the abnormal status of the operation. In this way the user can quickly perform a recovery process.

Furthermore, in the first embodiment described above, when the cassette 23 delivery operation by the oscillating member 81 is not performed normally, the cassette 23 delivery operation by the oscillating member 81 is executed again. since the re-executed operation (retry operation) eliminates the cause of the abnormally performed cassette 23 delivery operation by the oscillating member 81, the smear sample preparation operation of the smear sample preparation device 2 of the clinical specimen processing apparatus 1 is performed continuously without stopping. In this way the clinical specimen processing apparatus 1 is stopped a fewer number of times compared to when the clinical specimen processing apparatus 1 is stopped immediately when the cassette 23 delivery operation of the oscillating member 81 is not performed normally. As a result, sample processing time is faster, and the workload on the user performing the recovery process is lessened.

In the first embodiment, the redelivery operation of the cassette 23 from the origin position onto the conveyor belt 28b by the oscillating member 81 can be accomplished by returning the oscillating member 81 to the origin position before again executing the operation to deliver the cassette 23 by the oscillating member 81 based on detecting that the oscillating member 81 is not at the origin position (non-oscillated position) by means of the detection piece 81b and the sensor 88.

Second Embodiment

Figure 15:
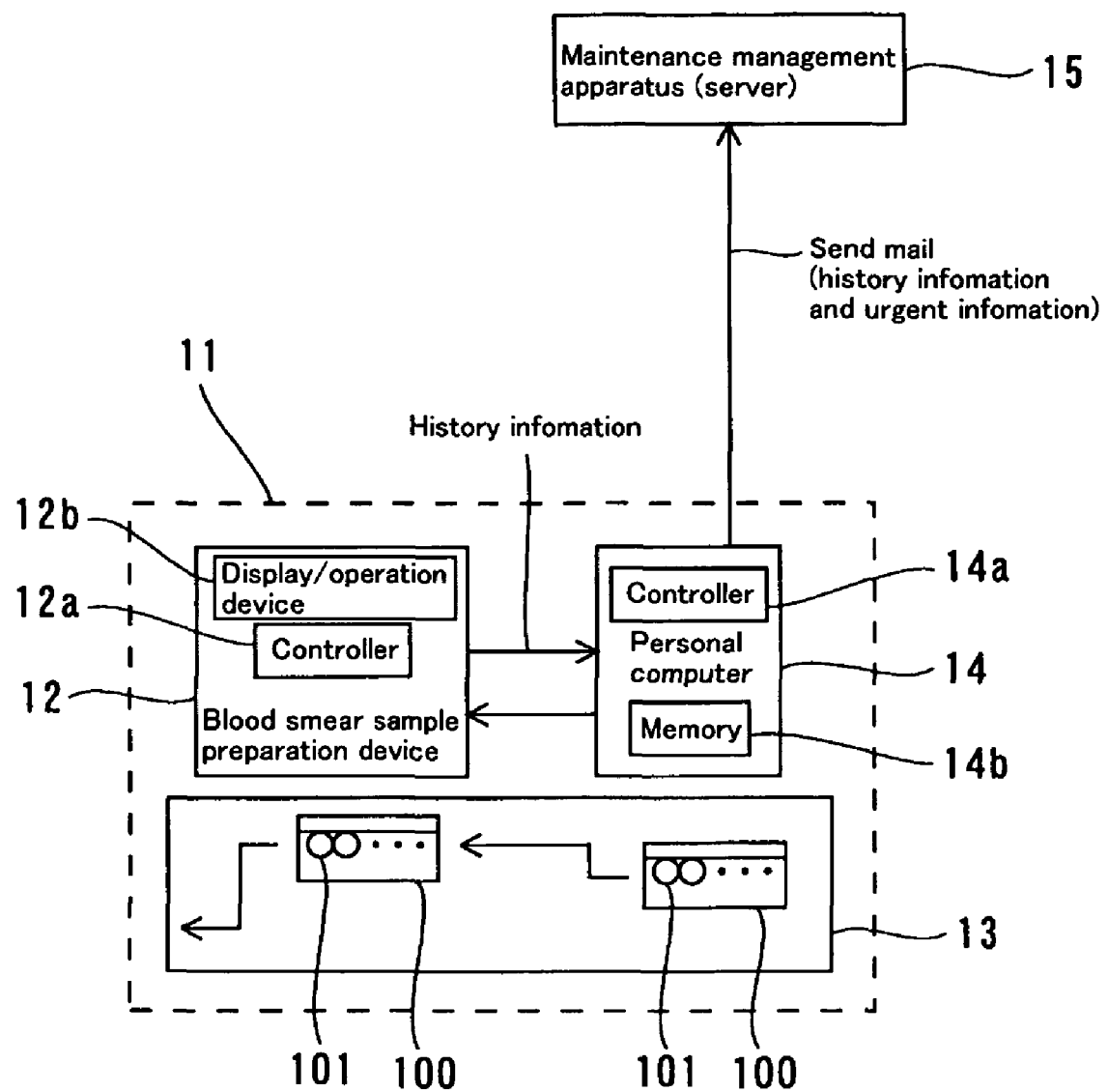
FIG. 15 is a block diagram showing the clinical specimen processing apparatus and off-site maintenance management device of a second embodiment of the present invention.

FIG. 15 is a block diagram of the clinical specimen processing apparatus and an off site maintenance management apparatus of the second embodiment of the present invention. Referring to FIG. 15, the clinical specimen processing apparatus 11 of the second embodiment of the present invention differs from the first embodiment in that the a personal computer 14 is connected to the blood smear sample preparation device 12 of the clinical specimen processing apparatus 11. The personal computer 14 is connected to a maintenance management apparatus (server) 15 installed at an off site maintenance company through a network. This network may be a special network such as a telephone line, the internet, LAN or the like.

The structure of the blood smear sample preparation device 12 and the conveyance device 13 of the second embodiment is such that the blood smear sample preparation device 12 has a controller 12a, and touch screen-type display/operation unit 12b. The controller 12a is identical to the controller 2a of the first embodiment with the exception that the control program (not shown in the drawing) contained in the ROM 20c is different; therefore, like parts are designated by like reference numbers, and their description is omitted. The blood smear sample preparation device 12 of the second embodiment transmits history information (error information and operation history information) from the blood smear sample preparation device 12 of the second embodiment to the personal computer 14.

The personal computer 14 includes an information processor, such as a controller 14a, and memory 14b as function blocks. The controller 14a has the function of determining whether or not error information sent by the controller 12a of the blood smear sample preparation device 12 is urgent information requiring urgent attention, and the function of sending history information (error history information and operation history information) and urgent information (information requiring urgent attention among the error information) of the blood smear sample preparation device 12 to the maintenance management apparatus (server) 15. The memory 14b has the function of storing the error history information and operation history information of the blood smear sample preparation device 12.

Figure 16:
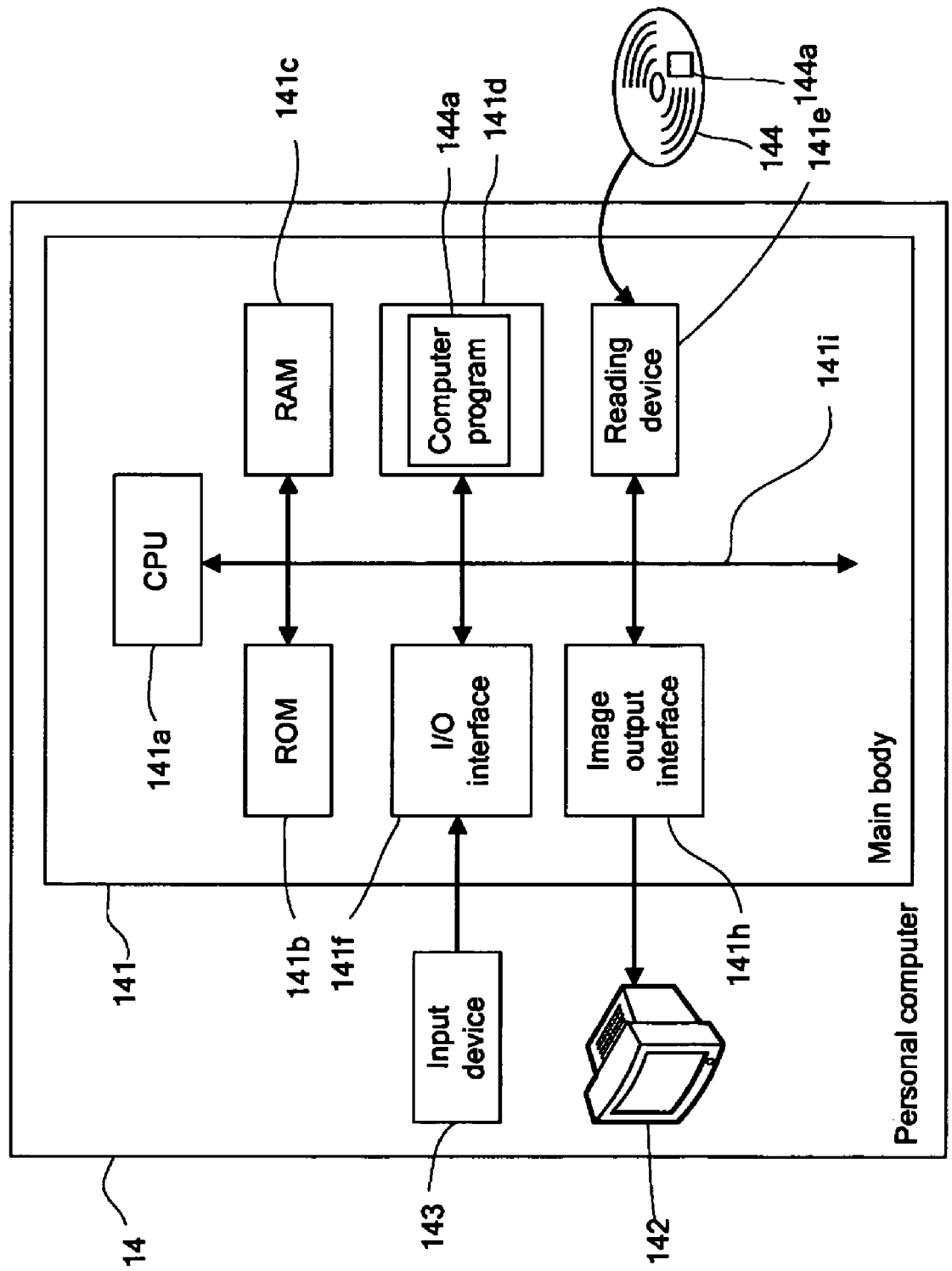
FIG. 16 is a block diagram showing the hardware structure of the personal computer of FIG. 15.

FIG. 16 is a block diagram showing the hardware structure of the personal computer 14 of FIG. 15. The personal computer 14 mainly includes a body 141, display 142, and input device 143. The body 141 mainly includes a CPU 141a, ROM 141b, RAM 141c, hard disk 141d, reading device 141e, I/O interface 141f, communication interface 141g, image output interface 141h; and the CPU 141a, ROM 141b, RAM 141c, hard disk 141d, reading device 141e, I/O interface 141f, and image output interface 141h are connected to a bus 141i to enable data communication.

The CPU 141a is capable of executing a control program stored in ROM 141b and a control program loaded in the RAM 141c. The controller 14a is realized as a function block when the CPU 141a executes an application program 144a described later.

The ROM 141b may be configured by a mask ROM, PROM, EPROM, EEPROM or the like, and stores the computer programs executed by the CPU 141a and the data used in such programs.

The RAM 141c is configured by an SRAM, DRAM or the like. The RAM 141c is used to read the computer program stored in ROM 141b or on the hard disk 141d. Furthermore, the RAM 141c is used as a work area for the CPU 141a when the computer programs are executed.

The hard disk 141d is used to install operating systems, application programs and the like, various types of computer programs executed by the CPU 141a, and data used in the execution of the computer programs. The application program 144a which is described later is also installed in the hard disk 141d. The hard disk 141d also stores an electronic mail client program (MUA) for sending, receiving, and processing electronic mail.

The reading device 141e is configured by a floppy disk drive, CD-ROM drive, DVD-ROM drive or the like, which is capable of reading the computer program and data recorded on a portable recording medium. The portable recording medium stores the application program 144a; the personal computer 14 reads the application program 144a of the present invention from the portable recording medium 144, and installs the application program 144a on the hard disk 141d.

The application program 144a can be provided over an electrical communication line from a device connected to the personal computer 14 externally so as to be capable of communication by means of an electrical communication line (wire line, wireless) without providing the application program 144a on a portable recording medium 14. For example, the application program 144a may be stored on a hard disk of a server computer on a network, such that the personal computer 14 can access the server computer and download the computer programs, and install the programs on the hard disk 141d.

An operating system providing a graphical user interface environment, such as, for example, Windows (registered trademark), a commercial product of Microsoft Corporation of the USA, or the like is installed on the hard disk 141d. In the following description, the application program 144a of the present embodiment operates in such an operating system.

The I/O interface 141f may be, for example, a serial interface such as a USB, IEEE1394, RS-232C or the like, a parallel interface such as SCSI, IDE, IEEE1284 or the like, or an analog interface such as such as a D/A converter, A/D converter or the like. The I/O interface 141f is connected to an input device 143 configured by a keyboard and mouse, such that a user may input data to the computer 14 using the input interface 143.

The image output interface 141h is connected to a device 142 such as an LCD, CRT or the like, so as to output image signals corresponding to image data received from the CPU 110a on the display 142. The display 142 displays the images (screens) in accordance with the input image signals.

Figure 17:
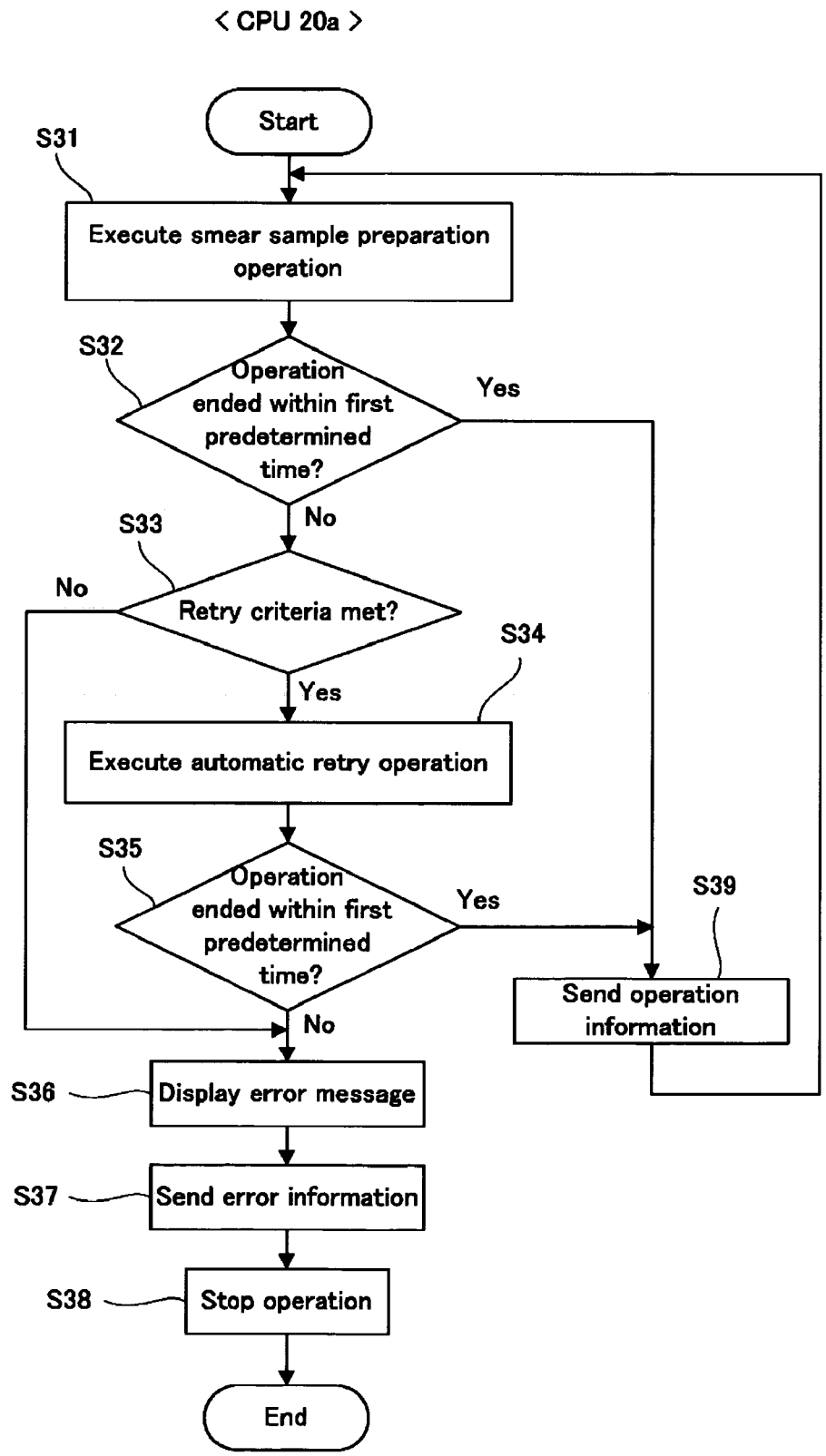
FIG. 17 is a flow chart illustrating the information transmission operation by the controller of the blood smear sample preparation device in the clinical specimen processing apparatus of the second embodiment shown in FIG. 15.
Figure 18:
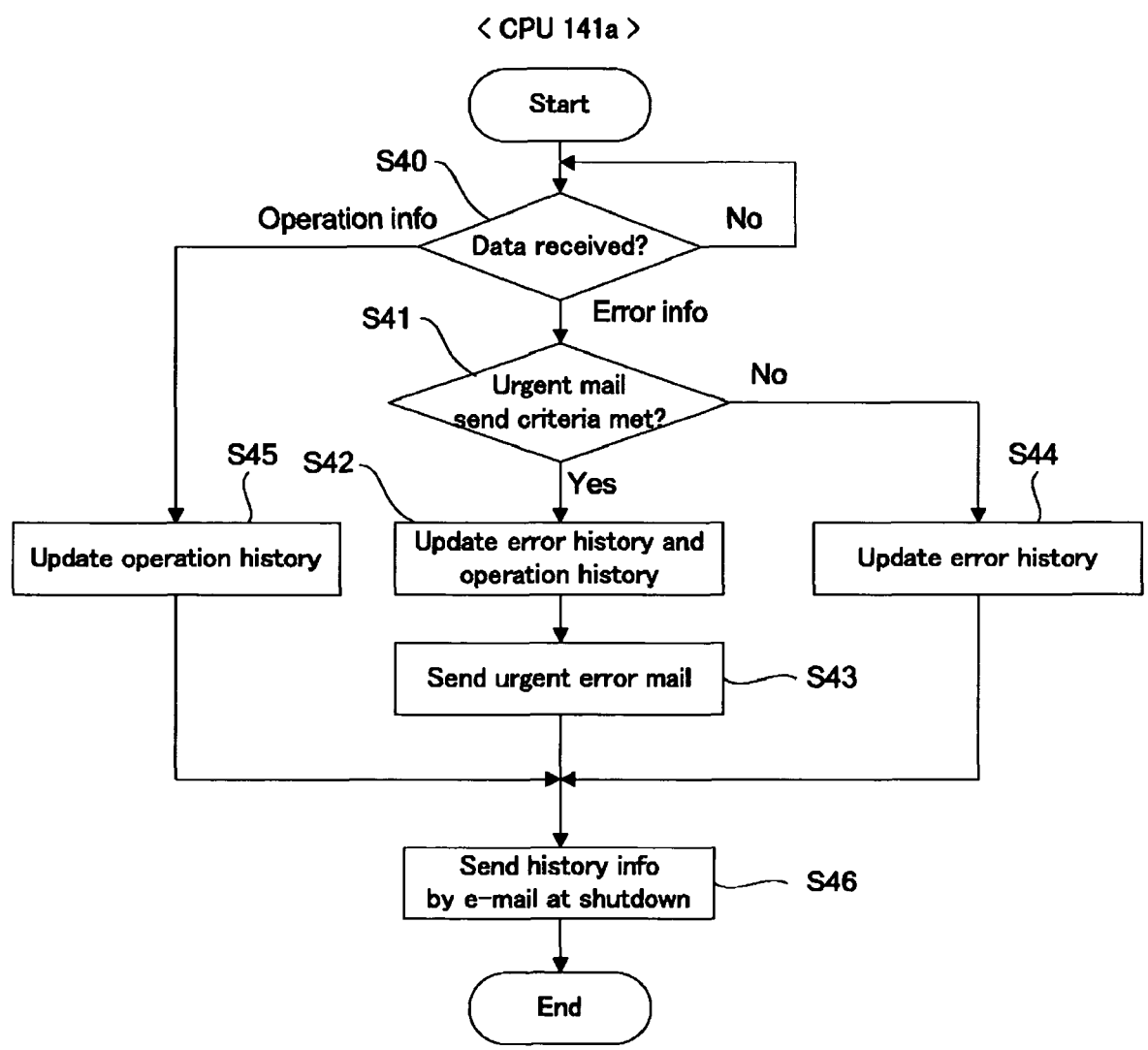
FIG. 18 is a flow chart illustrating the information transmission operation by the controller of the personal computer in the clinical specimen processing apparatus of the second embodiment shown in FIG. 15.

FIG. 17 is a flow chart illustrating the information transmission operation by the controller of the blood smear sample preparation device of the clinical specimen processing apparatus of the second embodiment shown in FIG. 15, and FIG. 18 is a flow chart illustrating the information transmission operation by the personal computer. The operation of the clinical specimen processing apparatus 11 of the second embodiment of the present invention is described below with reference to FIGS. 15~18. The clinical specimen processing apparatus 11 of the second embodiment displays error information of the blood smear sample preparation device 12 on the display/operation unit 2b, and transmits the history information (error information and operation history information) of the blood smear sample preparation device 12 to the personal computer 14. Furthermore, the controller 14a of the personal computer 14 transmits the history information (error history information and operation history information) of the blood smear sample preparation device 12, and urgent information (information requiring urgent attention among the error information) to the maintenance management apparatus (server) 15.

The information transmission operation by the controller 14a of the personal computer 14 and the controller 12a of the blood smear sample preparation device 12 is described below in detail with reference to the flow chart of FIG. 18. First, the CPU 20a of the blood smear sample preparation device 12 executes the smear sample preparation operation (step S31), and determines whether or not a predetermined part of the operation of the blood smear sample preparation device 12 ends within a first predetermined time set beforehand (step S32). When the operation of a predetermined part of the operation ends within a first predetermined time in step S32 (step S32: YES), the CPU 20a moves the process to step S39. When the predetermined part of the operation does not end within the first predetermined time in step S32 (step S32: NO), the CPU 20a determines whether or not the predetermined part of the operation belongs to the retry criteria (step S33). In the second embodiment, operations belonging to the retry criteria are, for example, the discharge pipette 71a and supply pipette 71b raising operation, and the operation of delivering the cassette 23 to the storage unit 28 by the input mechanism 28a of the first embodiment. When the predetermined part of the operation belongs to the retry criteria in step S33 (step S33: YES), the CPU 20a automatically executes a retry operation for the predetermined part of the operation (step S34). Then, the CPU 20a determines whether or not the predetermined part of the retry operation ended within a first predetermined time (step S35).

In the second embodiment, when the predetermined part of the retry operation has not ended within the first predetermined time in step S35, (step S35: NO), the CPU 20a display an error message on the display/operation unit 2b (step S36), sends error information to the personal computer 14 (step S37), stops the operation of the entire device (step S38), and ends the process. Even when the predetermined part pf the operation does not belong to the retry criteria (step S33: NO), the CPU 20a advances the process to step S36, displays the error message and sends error information to the personal computer 14. However, when the retry operation does end within the first predetermined time (step S35: YES), the CPU 20a generates operation information specifying the predetermined part of the operation has been executed, transmits the information to the personal computer 14 (step S39), and continues the on-going operation by returning the process to step S31.

Figure 19:
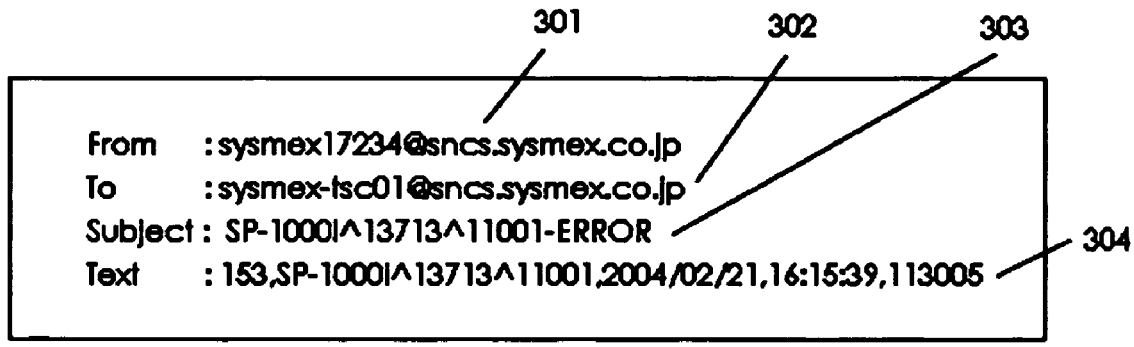
FIG. 19 is a structural diagram showing the content of the electronic mail which includes urgent information of the blood smear sample preparation device in the second embodiment.

The CPU 141a of the personal computer 14 waits to receive data (step S40), and when received data are error information ([error info] in step S40), determines whether or not the error information belongs to urgent electronic mail sending criteria (step S41). When the error information belongs to urgent electronic mail sending criteria (step S41: YES), the CPU 141a adds the received error information to the error history in the memory 14b, and adds information indicating an operation error to the operation history in the memory 14b (step S42), then sends urgent error mail to the maintenance management apparatus (sever) 15 (step S43). The CPU 141a then moves the process to step S46. In the second embodiment, an operation belonging to the urgent mail criteria is, for example, the cassette 23 delivery operation by the input mechanism 28a of the storage unit 28 described in the first embodiment. FIG. 19 is a schematic view showing an example of urgent error mail. The urgent error mail includes a sender mail address 301, destination mail address 302, subject 303, and text 304. The sender mail address 301 is the electronic mail address of the personal computer 14 associated with the maintenance system of the blood smear sample preparation device 12. The destination mail address 302 is the electronic mail address used by the maintenance company, for example, the electronic mail address of service personnel of the maintenance company. The mailbox of the destination mail address 302 is provided in the maintenance management apparatus 15. The subject 303 adds the text ERROR to the device ID, and it can be understood at a glance to be urgent information. The text 305 records a serial number (153), device ID (SP-1000iˆ13713ˆ11001), error generation date (2004/02/21), error generation time (16:15:39), error code (113005). The error code is a code associated with each error so as to specify the generated error. Therefore, since the information of the device ID, date, time, and error code are written directly in the text body, the urgent error mail can be received by the maintenance management apparatus 15 and quickly alerts the maintenance company of the abnormality. Furthermore, sending an urgent error mail to the portable terminal (personal computer node, portable telephone) of a service person from the maintenance company is particularly effective even though the portable terminal cannot open file attachments compared to alters by files attached to electronic mail since the information of the device ID, date, time, and error code are written directly in the text body.

When, on the other hand, the error information does not belong to urgent mail sending criteria in step S41 (step S41: NO), the CPU 141a adds the error information to the error history in the memory 14b (step S44), and the process moves to step S46. In the second embodiment, operations which do not belong to the urgent mail sending criteria include, for example, the discharge pipette 71a and supply pipette 71b raising operation described in the first embodiment. When the received data are operation data in step S40 (step S40: [OP INFO]), the CPU 141a sends the history information (operation history and error history) stored in the memory 14b to the maintenance management apparatus (server) 15 by electronic mail when the blood smear sample preparation device 12 shuts down (step S46), and the process ends.

In the history information transmission process at shutdown, all history information of the blood smear sample preparation device 12, including the history information requiring urgent attention (urgent information), is sent from the personal computer 14 to the maintenance management apparatus (server) 15 over the network. The history information of the blood smear sample preparation device 12 is prepared as a file attachment for each type of history information by the CPU 141a, and sent as a file attachment via electronic mail. The types of history information of the blood smear sample preparation device 12 include, for example, an error log indicating the error information history of the blood smear sample preparation device 12, operation count specifying the number of operations such as number of smears and number of staining, and maintenance parts and replaced parts specifying the numbers of maintenance and replaced parts. The device ID, date, time, error code and like information of each abnormality are included in the file attachment in the case of an error log specifying the abnormal history of the smear sample preparation device 12. Furthermore, date, time, smear and stain operation categories, and number of operations are included in the file attachment for operation count.

Figure 20:
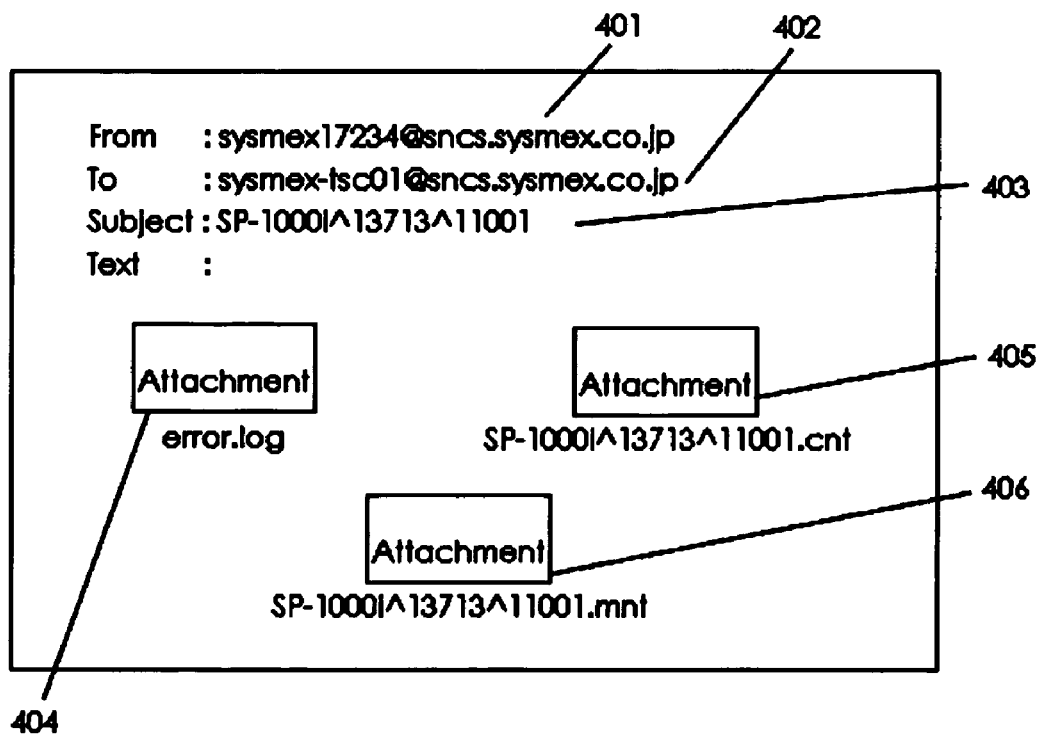
FIG. 20 is a structural diagram showing the content of the electronic mail which includes operation information of the blood smear sample preparation device in the second embodiment.

FIG. 20 is a schematic view showing an example of electronic mail file attachment containing history information. As shown in FIG. 20, this electronic mail includes a sender mail address 401, destination mail address 402, subject 403, error log file attachment 404, operation count file attachment 405, and maintenance part and replaced parts log file attachment 406. The sender mail address 401 and destination mail address 402 are identical to the urgent error mail sender mail address 301 and destination address 302. The subject 403 contains the device ID, such that the subject device is readily understood. As shown in FIG. 21, the error log file attachment 404 is a table configured by a serial number 501, device ID number 502, error generation date 503, error generation time 504, error code 505. As shown in FIG. 22, the operation count file attachment 405 is a table configured by operation date 511, operation time 512, category 513, and number of operations 514. The categories 513 represent the types of operations. As shown in FIG. 23, the maintenanced parts and replaced parts log file attachment 406 is a table configured by replacement date 521, replacement time 522, and maintenanced parts and replaced parts information 523. The maintenanced parts and replaced parts information 523 represents the replaced part, such as ink ribbon, buffer solution, drawing glass and the like. Thus, by dividing the error content by error code, the error classification can be easily understood and the error frequency can be readily understood by the error code 505. Furthermore, the operation number of each part of the device is understood from the classification 513, and breakdowns can be predicted from the operation count. Furthermore, which parts have been replaced can be understood from the maintenanced parts and replaced parts information 523, and next replacement date can be predicted. A large volume of data can be sent by electronic mail notification in the file attachment format, the file attachment can be read by commercial spreadsheet software so as to effectively process large amounts of data.

In the second embodiment, when an error is determined after a retry operation (redelivery operation to deliver the cassette 23 by the oscillating member 81 of the input mechanism 28a, or re-raising operation to raise the discharge pipette 71a and supply pipette 71b), a user can immediately confirm the retry operation error (abnormality) by the error information displayed on the display/operation unit 12b.

In the second embodiment, abnormalities requiring urgent attention receive prompt maintenance since the maintenance company at which the maintenance management apparatus (server) 15 is installed is immediately alerted to the abnormality by the error information requiring urgent attention, among the error information determined as an error after a retry operation, being sent to the maintenance management apparatus (server) 15 over the network. When an error requiring urgent attention is not generated, the history information of the blood smear sample preparation device 12 can be sent periodically to the maintenance management apparatus (server) 15 by sending the error history and operation history to the maintenance management apparatus (server) 15 when the blood smear sample preparation device 12 shuts down.

The disclosed embodiments are not to be considered as being limited to the above examples. The scope of the present invention is determined by the scope of the claims and not by the illustrations of the embodiments, and includes all modifications within the scope of the claims and all equivalences therein.

For example, in the above embodiments, the present invention has been described by way of examples applied to clinical specimen processing apparatuses including a blood smear sample preparation device, however, the present invention is not limited to this application inasmuch as the invention is also applicable to other clinical specimen processing apparatuses. For example, the present invention is applicable to blood corpuscle analyzers (blood analyzers) which analyze the blood cell count, hematocrit, or hemoglobin or the like of a blood sample, immunoassay devices which determine the concentration of antibodies or antigens of cancer markers and infection, blood coagulation measuring devices which detect the coagulation function of serum or plasma samples, biochemical analyzers which measure enzyme activity if indicators of organ function and serum total protein, urine analyzers which determine the presence/absence of white cells, sugar, and proteins in urine specimens, and clinical specimen processing devices such as urine sedimentation analyzers which quantify bacteria columnar epithelium, dermal cells, and red blood cells.

The above embodiments describe examples of retry operations for a cassette delivery operation performed by an oscillating member of an input mechanism of a storage unit, and a discharge pipette and supply pipette raising operation, however, the present invention is not limited to these retry operations inasmuch as retry operations for operations performed by other operating members of the blood smear sample preparation device are also possible. For example, retry operations are also possible for the raising operation and lowering operation of the discharge pipette and supply pipette of the suction/discharge units other than the third suction/discharge unit of the staining unit, and the cassette delivery operation of the oscillating member of the input mechanism of the staining unit.

Although the display/operation unit is used as an example of the notification means of the present invention for alerting a user to abnormality information after a retry operation, the present invention is not limited to this example inasmuch as other notification means, such as sound-emitting speakers, or light-emitting flashing light source, also may be used in place of the display/operation unit.

In the example of the second embodiment, non-urgent error history information, among error information determined after a retry operation, and operation history information (retry operation history and origin return operation history) are sent to the maintenance management apparatus (server) when the blood smear sample preparation device is shut down. However, the present invention is not limited to this example inasmuch as non-urgent error history information and operation history information may be sent to the maintenance management apparatus (server) when the blood smear sample preparation device is started.

Although error information of the raising operation of the discharge pipette and supply pipette are stored in the memory of the personal computer as error history information which does not belong to urgent error mail sending criteria in the example of the second embodiment, the present invention is not limited to this example inasmuch as error information of the raising operation of the discharge pipette and supply pipette also may be sent to the maintenance management apparatus (server) as error history information belonging to the urgent error mail sending criteria by the controller of the personal computer.

Although urgent information (urgent error mail) is sent to the maintenance management apparatus (server) of the maintenance company in the second embodiment, the present invention is not limited to this example inasmuch as urgent information (urgent error mail) also may be sent to a platform-type personal computer, and portable telephone of service personnel of the maintenance company. In this case, the platform-type personal computer and portable telephone of service personnel of the maintenance company are equivalent to the [maintenance management apparatus] of the present invention.

Although the history information and urgent information are sent to the maintenance management apparatus (server) by electronic mail in the example of the second embodiment, the present invention is not limited to this example inasmuch as the history information and urgent information also may be sent to the maintenance management apparatus (server) by data communication methods other than electronic mail.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

It is therefore intended that the foregoing detailed description be regarded as illustrative rather than limiting, and that it be understood that it is the following claims, including all equivalents, that are intended to define the spirit and scope of this invention.

What is claimed is:

1. A clinical specimen processing apparatus comprising:
    a mechanism that performs a predetermined operation to process a clinical specimen, wherein the mechanism comprises an object used for performing the predetermined operation and a detection piece which moves in conjunction with the object;
    a sensor that detects the detection piece when the object is at a predetermined position, wherein the sensor comprises a light transmitting type sensor; and
    a controller that is in communication with the mechanism and the sensor, the controller configured to control the mechanism so that the mechanism executes the predetermined operation beginning from a first initial time, wherein the controller controls the mechanism during the predetermined operation in such a manner that the controller will re-execute the predetermined operation at a second initial time should the sensor fail to detect the detection piece when the object is at the predetermined position after a predetermined time as measured from the first initial time has elapsed.

2. The clinical specimen processing apparatus of claim 1, wherein the controller stops the mechanism from re-executing the predetermined operation if the sensor fails to detect the detection piece when the object is at the predetermined position when a second predetermined time as measured from the second initial time has elapsed.

3. The clinical specimen processing apparatus of claim 2, comprising a display, wherein the controller sends error information to be shown on the display if during the re-executing the predetermined operation the sensor has not detected the detection piece when the object is at the predetermined position when the second predetermined time from the second initial time has elapsed.

4. The clinical specimen processing apparatus of claim 1, wherein the controller controls the mechanism so as to move the object to an initial position before re-executing the predetermined operation.

5. The clinical specimen processing apparatus of claim 1, wherein the controller determines that the predetermined operation is in an abnormal state during the re-executing of the predetermined operation if the sensor has not detected the detection piece when the object is at the predetermined position when a third predetermined time as measured from the second initial time has elapsed.

6. The clinical specimen processing apparatus of claim 1, comprising:
    a specimen holding member; and
    a second sensor in communication with the controller, the second sensor detects whether the specimen holding member has been moved by the object to a second predetermined position, wherein the second sensor comprises a light reflecting type sensor.

7. The clinical specimen processing apparatus of claim 1, wherein the object comprises a pipette.

8. The clinical specimen processing apparatus of claim 1, wherein the object comprises an oscillator.

9. The clinical specimen processing apparatus of claim 3, comprising an information processor in communication with the controller, the information processor is configured to transmit the error information to a maintenance management apparatus installed off site.

10. The clinical specimen processing apparatus of claim 9, wherein the information processor is configured to transmit operation information relating to the predetermined operation to the maintenance management apparatus.

11. The clinical specimen processing apparatus of claim 9, wherein the information processor is configured to transmit the error information to the maintenance management apparatus using electronic mail.

12. The clinical specimen processing apparatus of claim 9, wherein the information processor is configured to 1) transmit the error information to the maintenance management apparatus by electronic mail with a predetermined timing, and 2) transmit urgent information requiring urgent action in the error information to the maintenance management apparatus by electronic mail without waiting for the predetermined timing.

13. The clinical specimen processing apparatus of claim 10, wherein the information processor is configured to transmit the error information and the operation information to the maintenance management apparatus by electronic mail when starting or at shut down.

* * * * *